US012800533B2

(12) United States Patent
Zhao et al.

(10) Patent No.: US 12,800,533 B2
(45) Date of Patent: Nov. 17, 2026

(54) DEVICE AND METHOD FOR SENSING A TARGET GAS

(71) Applicant: Infineon Technologies AG, Neubiberg (DE)

(72) Inventors: Jianyu Zhao, Munich (DE); Cecilia Carbonelli, Munich (DE); Simon Mittermaier, Forstern (DE); Yosra Bahri, Munich (DE)

(73) Assignee: Infineon Technologies AG, Neubiberg (DE)

( * ) Notice: Subject to any disclaimer, the term of this patent is extended or adjusted under 35 U.S.C. 154(b) by 377 days.

(21) Appl. No.: 18/506,556

(22) Filed: Nov. 10, 2023

(65) Prior Publication Data

US 2024/0159698 A1 May 16, 2024

(30) Foreign Application Priority Data

Nov. 11, 2022 (EP) .................................... 22207064

(51) Int. Cl.
*G01N 27/12* (2006.01)
*G01N 33/00* (2006.01)

(52) U.S. Cl.
CPC ......... *G01N 27/12* (2013.01); *G01N 33/0027* (2013.01)

(58) Field of Classification Search
CPC ............... G01N 27/12; G01N 33/0006; G01N 33/0027; G01N 33/0062; G01N 33/0009
See application file for complete search history.

(56) References Cited

U.S. PATENT DOCUMENTS

| | | | | |
|---|---|---|---|---|
| 6,311,480 | B1 * | 11/2001 | Suzuki | F01N 13/011 60/276 |
| 10,551,356 | B2 * | 2/2020 | Tumpold | G01N 29/2418 |
| 2021/0285907 | A1 * | 9/2021 | Makaram | G01N 27/122 |
| 2022/0011266 | A1 * | 1/2022 | Liu | G01N 27/66 |

OTHER PUBLICATIONS

Haugen et al., "A calibration method for handling the temporal drift of solid state gas-sensors," Analytica Chimica Acta, vol. 407, No. 1-2, Feb. 1, 2000 (Feb. 1, 2000), pp. 23-39, XP055152962, 17 pages.

Hossein-Babaei et al., "Compensation for the drift-like terms caused by environmental fluctuations in the responses of chemoresistive gas sensors," Sensors and Actuators B: Chemical, Elsevier BV, NL, vol. 143, No. 2, Jan. 7, 2010 (Jan. 7, 2010), pp. 641-648, XP026821488, 8 pages.

* cited by examiner

*Primary Examiner* — Stephen D Meier
*Assistant Examiner* — Quang X Nguyen
(74) *Attorney, Agent, or Firm* — Slater Matsil, LLP

(57) ABSTRACT

A gas sensing device for sensing a target gas in a gas mixture comprises: a measurement module configured for obtaining a sampled measurement signal, the sampled measurement signal being responsive to a concentration of the target gas in the gas mixture; a compensation module configured for compensating the sampled measurement signal using an offset information to obtain a compensated measurement signal; a processing module configured for detecting a sample of the sampled measurement signal, which sample fulfils a set of one or more criteria, and wherein a first criterion of the set of criteria is fulfilled if, according to an evaluation of the sampled measurement signal, the sample is associated with a concentration of the target gas below a threshold, and updating the offset information based on a sample which fulfills the set of criteria.

20 Claims, 16 Drawing Sheets

DEVICE AND METHOD FOR SENSING A TARGET GAS

This application claims the benefit of European Patent Application No. 22207064.1, filed on Nov. 11, 2022, which application is hereby incorporated herein by reference.

TECHNICAL FIELD

Examples of the present disclosure are concerned with a gas sensing device. Further examples relate to a method for sensing a target gas. Some embodiments relate to an automatic base line correction for multichannel gas sensors.

BACKGROUND

Gas sensing devices are used for sensing one or more target gases in a gas mixture, for example, for determining a concentration of a target gas in the gas mixture. To this end, gas sensing devices may obtain a measurement signal which is responsive to the concentration of the target gas in the gas mixture. The response of the measurement signal to the target gas is often prone to degradation or, in general, temporal variations which are not caused by a change of the concentration of the target gas. Such variations may be referred to as sensor drift. For example, chemical sensors are small devices that convert chemical information, e.g., a concentration, into measurable electronic signals. If deployed in the field for a long time, such sensors are often prone to small and non-deterministic temporal variations of the sensor response when it is exposed to the same analytes under the same conditions, which is referred to as sensor drift. The resulting change in the sensor signals may influence the quality of the estimated concentration over time.

SUMMARY

Accordingly, a concept for gas sensing is desirable, which provides a high accuracy over a long operation time is provided by the gas sensing device and the methods and operations disclosed herein.

Examples of the present disclosure rely on the idea that a drift of an offset of a measurement signal may be compensated on the basis of measurement data obtained at a time instance at which the concentration of the target gas is particularly low or zero, i.e., below a threshold. This finding is exploited by examples of the present disclosure by detecting a sample of a sampled measurement signal, for which sample the concentration of the target gas is below a threshold according to an evaluation of the measurement signal. Detecting samples, for which the concentration of the target gas is below the threshold, allows using the sample, or a measurement value associated with the sample, for updating an offset, which is used for compensating the measurement signal. Accordingly, the offset may be updated without relying on external data such as information provided by a reference sensor. Therefore, the disclosed concept allows for an independent long term operation of a sensing device, e.g., independent of reference data and/or independent of a connectivity to an external data provider.

Examples of the present disclosure provide a gas sensing device for sensing a target gas in a gas mixture, the gas sensing device comprising: A measurement module configured for obtaining a sampled measurement signal, the sampled measurement signal being responsive to a concentration of the target gas and the gas mixture; a compensation module configured for compensating the sampled measurement signal using an offset information to obtain a compensated measurement signal; a processing module configured for detecting a sample of the sampled measurement signal, which sample fulfils a set of one or more criteria, wherein a first criterion of the set of criteria is fulfilled if, according to an evaluation of the sampled measurement signal, the sample is associated with a concentration of the target gas below a threshold, and wherein the processing module is configured for updating the offset information based on a sample, which fulfils the set of criteria.

Further examples of the present disclosure provide a method for sensing a target gas in a gas mixture, the method comprising: obtaining a sampled measurement signal, the sampled measurement signal being responsive to a concentration of the target gas in the gas mixture. The method includes compensating the sampled measurement signal using an offset information to obtain a compensated measurement signal, detecting a sample of the sampled measurement signal, which sample fulfils a set of one or more criteria, where a first criterion of the set of criteria is fulfilled if, according to an evaluation of the sampled measurement signal, the sample is associated with a concentration of the target gas below a threshold, and updating the offset information based on a sample which fulfills the set of criteria.

BRIEF DESCRIPTION OF THE DRAWINGS

Examples of the present disclosure are described in more detail below with respect to the figures, among which.

DETAILED DESCRIPTION OF ILLUSTRATIVE EMBODIMENTS

Examples of the present disclosure are now described in more detail with reference to the accompanying drawings, in which the same or similar elements or elements that have the same or similar functionality have the same reference signs assigned or are identified with the same name. In the following description, a plurality of details is set forth to provide a thorough explanation of examples of the disclosure. However, it will be apparent to one skilled in the art that other examples may be implemented without these specific details. In addition, features of the different examples described herein may be combined with each other, unless specifically noted otherwise.

Figure 1:
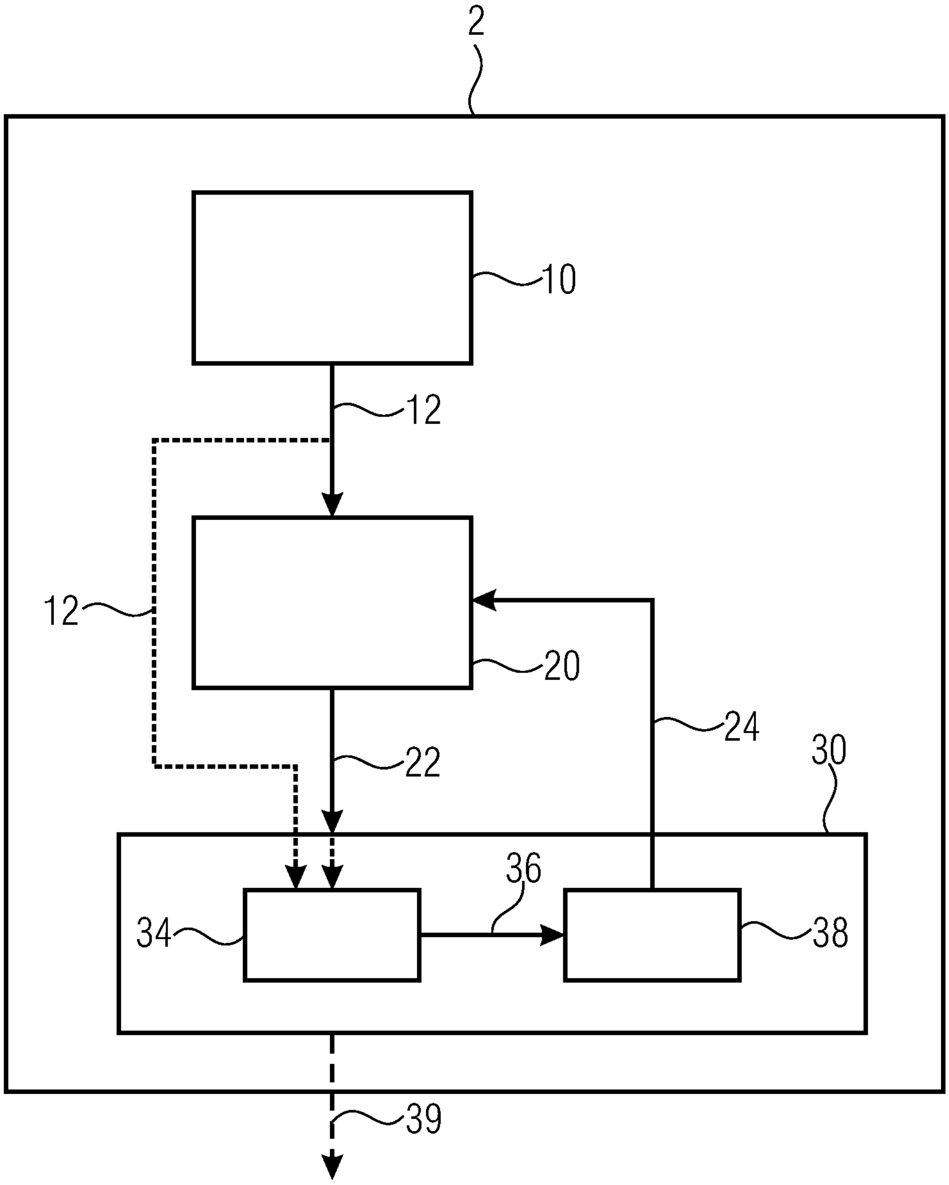
FIG. 1 illustrates an example of a gas sensing device and an example of a method for sensing a target gas according to the present disclosure.

FIG. 1 illustrates an example of a gas sensing device 2 for sensing a target gas in a gas mixture according to the present disclosure. The gas sensing device 2 comprises a measurement module 10, a compensation module 20, and a processing module 30. The measurement module 10 is configured for obtaining a sampled measurement signal 12, which is responsive to a concentration of the target gas in the gas mixture. The compensation module 20 is configured for compensating (or calibrating), e.g., normalizing or offsetting, the sampled measurement signal 12 using an offset information 24, e.g., an offset value, or a base line value, to obtain a compensated measurement signal 22. The processing module 30 comprises a detection block 34 (or detection module) configured for detecting a sample of the sampled measurement signal 12, which sample fulfils a set of one or more criteria. The set of criteria comprises a first criterion, which is fulfilled if, according to an evaluation of the sampled measurement signal (e.g., an evaluation of the compensated measurement value), the sample is associated with a concentration of the target gas below a threshold, e.g., a predetermined threshold. The processing module 30 further comprises an updating block 38 (or updating module) configured for updating the offset information based on a sample 36, which fulfils the set of criteria, e.g., a sample detected in block 34. A sample, which fulfils the set of criteria may be referred to as a detected sample in the following.

For example, the measurement module 10 may receive the sampled measurement signal 12 from a sensing module, which is attached to or connected with the gas sensing device 2, in particular the measurement module 10. Alternatively, the measurement module 10 may comprise a sensing module for measuring and/or providing the sampled measurement signal 12.

For example, each of a plurality of samples of the sampled measurement signal 12 may be associated with a respective time instance. The sampled measurement signal 12 may comprise, for each of the samples, one or more measurement values. For example, each of the one or more measurement values may represent a resistance or a conductance of a sensing layer of a respective one of one or more sensing units, e.g., as described with respect to FIG. 2. In other words, the measurement module 10 may provide the sampled measurement signal 12 based on respective measurement signals provided by one or more sensing units, e.g., chemo-resistive sensing units.

For example, the compensation module 20 compensates a drift or an offset in the sampled measurement signal, e.g., an offset or a drift inherent to the one or more measurement values of the samples of the sampled measurement signal 12, using the offset information 24. For example, the offset information comprises an offset value, which may also be referred to as a base line value. For example, the compensation module 20 subtracts the offset value from the measurement values to obtain compensated measurement values of respective samples of the compensated measurement signal 22.

For example, the compensated measurement signal 22 comprises a plurality of samples, each comprising one or more compensated measurement values. For example, each sample of the compensated measurement values may be obtained based on one or more samples of the sampled measurement signal 22. In examples, the compensated measurement signal comprises, for each of, or for all of, or for each of a portion of the samples of the sampled measurement signal 12 one or more compensated measurement values obtained by subtracting an offset value of the offset information 24 from respective measurement values of the sampled measurement signal. It is noted that the compensation of the sampled measurement signal 12 performed by compensation module 20 may comprise further operations, such as a normalization. For example, the difference between a measurement value of the sampled measurement signal 12 and the offset value may be normalized, e.g., divided by, the offset value to obtain a compensated measurement value of a corresponding sample of the compensated measurement signal 22.

For example, the detection block 34 may check, for each of the samples of the sampled measurement signal 12, or a subset thereof, or for each of the samples of the compensated measurement signal 22, or a subset thereof, if the respective sample fulfils the one or more criteria. If the sample fulfils the one or more criteria, the updating block 38 may use the sample, e.g., the one or more measurement values, or the one or more compensated measurement values, associated with the respective sample, for updating the offset information 24. In other words, the detection of a sample fulfilling the one or more criteria may trigger an update of the offset information 24.

In other words, the sampled measurement signal 22 may comprise a sequence of samples and the processing module 30 may check, for a subset of samples of the sequence, or for all samples of the sequence, whether the set of one or more criteria is fulfilled.

For example, the processing module 30, or the updating block 38, may use the measurement value associated with the detected sample 36 as an offset value. In other words, the processing module 30 may substitute an offset value of the offset information 24 with the measurement value of the detected sample 36.

For example, the evaluation of the sampled measurement signal 20, based on which the sample detection 34 is performed, may be performed by the processing module 30. As illustrated in FIG. 1, the evaluation may be performed directly on the sampled measurement signal 12, or alternatively, on the compensated measurement signal 22 derived from the sampled measurement signal 12. In other words, the evaluation of the sampled measurement signal 20, based on which the sample detection 34 is performed, may in examples include the compensation performed by compensation module 20. Furthermore, the evaluation may optionally be part of determining a sensing result, e.g. as described with respect to FIG. 10, FIG. 15, or FIG. 16.

Accordingly, in examples, the detection 34 may be performed on a sensing result, or may be performed based on information obtained during the determination of a sensing result.

For example, the first criterion is not fulfilled if according to an evaluation of the sampled measurement signal, the sample is not associated with a concentration of the target gas below a threshold, e.g., a predetermined threshold.

For example, the threshold for the concentration of the target gas may be a predetermined threshold, or may be adaptive, e.g. may be adapted in accordance with a current state of operation, or in accordance with a model used for obtaining a sensing result based on the compensated measurement signal 22.

For example, the threshold may be a low concentration threshold. That is, a concentration below the threshold may represent, according to the evaluation of the sampled measurement signal (e.g., an evaluation of the compensated measurement value), a small concentration or a zero concentration. For example, the threshold is 5% or 1% of the measurement range for the concentration of the target gas. In examples, the threshold is zero. In particular, in cases in which the compensation 20 includes a subtraction of an offset value from the measurement values to obtain the compensated measurement values, the threshold may be zero, or may be 1% of a maximum concentration associated with a measurement range for the concentration of the target gas. In case of a compensation based on a difference between the measurement values and the offset value, negative values of the compensated measurement values may indicate a drift of the base line of the measurement signal. Using the measurement values of a sample, for which the compensated measurement value is negative, a new offset value may compensate for a drift of the offset value.

According to examples, the processing module 30 uses an algorithm or an algorithmic module, e.g., a machine learning algorithm or a machine learning model to determine a sensing result, e.g., a value representing the concentration of the target gas, based on the compensated measurement signal 22.

According to examples, the processing module 30 performs the evaluation of a compensated measurement signal 22 with respect to a characteristic of the compensated measurement signal 22, e.g., a predetermined characteristic. According to this example, the first criterion is fulfilled if the characteristic indicates that the sample is associated with the concentration of the target gas below the threshold, e.g., the predetermined threshold.

For example, the characteristic of the compensated measurement signal is a measurement value of the compensated measurement signal.

It is noted that FIG. 1 may also serve as an illustration for a method for sensing a target gas in a gas mixture according to an example of the present disclosure. In this respect, the modules 10, 20, 30, and blocks 34, 38 may be regarded as blocks of a block diagram describing the method for sensing a target gas, and the functionalities provided by the modules may be regarded as steps of the method. Accordingly, an example of the present disclosure provides a method for sensing a target gas in a gas mixture, the method comprising a step 10 of obtaining a sampled measurement signal 12, the sampled measurement signal 12 being responsive to a concentration of the target gas in the gas mixture; a step 20 of compensating the sampled measurement signal 12 using an offset information 24 to obtain a compensated measurement signal 22; a step of detecting 34 a sample 36 of the sampled measurement signal 12, which sample 36 fulfils a set of one or more criteria, wherein a first criterion of the set of criteria is fulfilled if, according to an evaluation of the sampled measurement signal 12 (e.g., an evaluation of the compensated measurement signal 22), the sample 36 is associated with a concentration of the target gas below a threshold; and a step 38 of updating the offset information 24 based on a sample 36 which fulfils the set of criteria.

Figure 2:
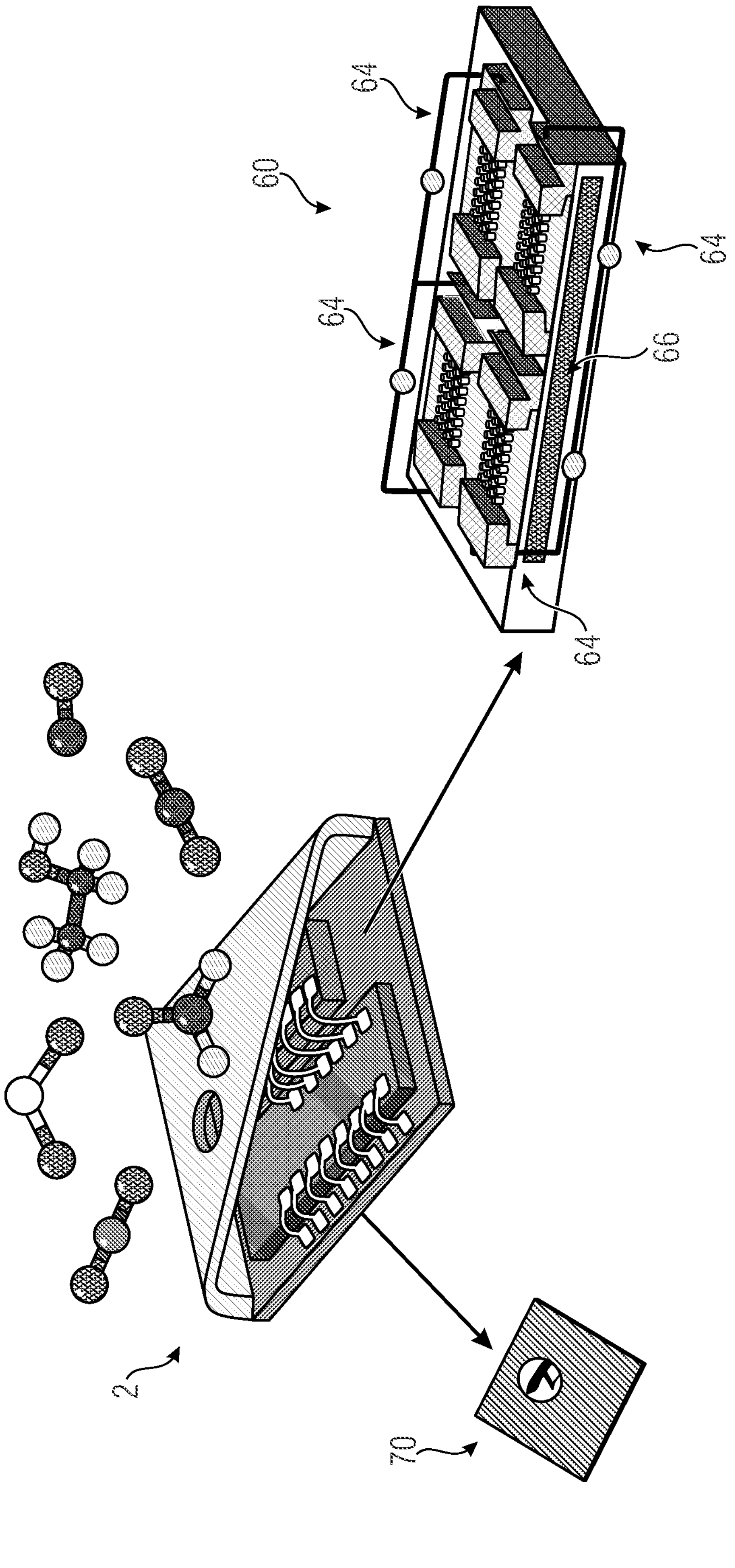
FIG. 2 illustrates an example of a gas sensing device with a chemo-resistive gas sensing module according to the present disclosure.

FIG. 2 illustrates another example of a gas sensing device 2. For example, the gas sensing device 2 of FIG. 1 may optionally be implemented as described with respect to FIG. 2. According to the example of FIG. 2, the gas sensing device 2 comprises a multi-gas sensor 60. For example, the multi-gas sensor 60 may be part of the measurement module 10 of FIG. 1. The multi-gas sensor 60 comprises a set of one or more chemo-resistive sensing units 64. For example, each of the sensing units 64 comprises a sensing layer, which is exposed to the gas mixture in the environment of the gas sensing device 2 during operation. During operation, gas molecules of the gas mixture may adsorb to the sensing layer, inducing a change of an electronic resistance (or conductance) of the sensing layer, which is measured by the sensing unit to provide a measurement signal. For example, the multi-gas sensor **6*o* may comprise four sensing units 64**. For example, the sensing layer may be carbon based or graphene based, however, other implementations of chemo resistive sensing units are possible.

For example, the sensing layers of the sensing units of the multi-gas sensor **6*o* may be functionalized with different chemicals for dissimilar selectivity. For example, graphene based sensing fields of the multi-gas sensor 6*o*** may be functionalized with metallic elements Pd, Pt, and Fe, respectively or combinations thereof. The different functionalization may result in different types of gas molecules to be preferably adsorbed at the sensing layer and/or may result in different sensor responses in the presence of specific gasses.

In other words, the interaction between the sensing layer, e.g., the graphene sheets, and the absorbed gas may influence the electronic structure of the material of the sensing layer, resulting in an altered charge carrier concentration in the sensing layer and a changed electrical resistance of the sensing layer, which can be measured. Due to different functionalizations of different sensing layers of the multi-gas sensor 60, and the resulting different sensitivities toward various gas molecules, the resistances of the sensing layers may change in disparate patterns, making it possible to analyze complicated gas mixtures with one single sensor array.

Accordingly, the sampled measurement signal 12 may comprise, for each sample, a measurement value, e.g. a resistance value or conductance value, for each of a plurality of chemo-resistive sensing units 64.

The multi-gas sensor 60 may optimally further comprise a heater 66. The heater 66 may be employed for desorbing adsorbed gas molecules from a surface of the sensing layers to avoid saturation of the sensing layers, e.g., the graphene layers, with gas molecules. In other words, the heater 66 may be used for heating the sensing units 64, or the sensing layers of the sensing units 64, to induce gas molecules on the sensing layers to desorb from the surface of the sensing layers. After heating, e.g., after a heating cycle for desorbing molecules from the surface, the heater may be adjusted to a lower power, which again allows molecules to be adsorbed. Additionally or alternatively, the heater 66 may be used for exposing the sensing layers of the sensing units 64 to temporally varying temperature profiles. To this end, the heating temperature may be controlled following a predetermined wave form, e.g., a square wave or a sinusoidal wave. Exposing the sensing layers to a wave form may introduce a corresponding dynamic to the measurement signals of the sensors, which may be exploited in evaluating the measurement signals.

In other words, the processing unit 30 may evaluate the measurement signal using data processing techniques based on the wave form of the temperature profile, to which the sensing layers are exposed. Operating modes with square wave and sinusoidal waves may be referred to as pulse modes and sine modes, respectively, in the following.

As illustrated in FIG. 2, the gas sensing device 2 may further comprise a signal processor 70. Signal processor 70, e.g. a microcontroller, may implement the compensation module 20 and the processing module 30, including blocks 30 and 38, and optionally also part of the measurement module 10. For example, the measurement module 10 may be partially implemented by the signal processor 70 and the multi-gas sensor 60. For example, the signal processor 70 may sample measurement signals provided by the multi-gas sensor 60. For example, the signal processor 70 may be a programmable system on a chip (PSoC), e.g., an Infineon PSoC®, or an application specific integrated circuit (ASIC). In examples, the multi-gas sensor 60 may be implemented as a microelectronic mechanical system (MEMS) device.

In other words, referring to the gas sensing device of FIG. 1, according to examples, the sampled measurement signal 12 may be indicative of a resistance, or a conductance, of a chemo-resistive gas sensing unit, e.g., the gas sensing unit 64 as described with respect to FIG. 2. The characteristic, e.g., the predetermined characteristic, with respect to which the compensated measurement signal 22 may be evaluated for the detection 34, may, according to this example, be a sign and/or a magnitude of the compensated measurement signal 22. The sign and/or the magnitude of the compensated measurement signal may provide a reliable estimate of whether the concentration of the target gas is below the threshold or not.

Figure 3:
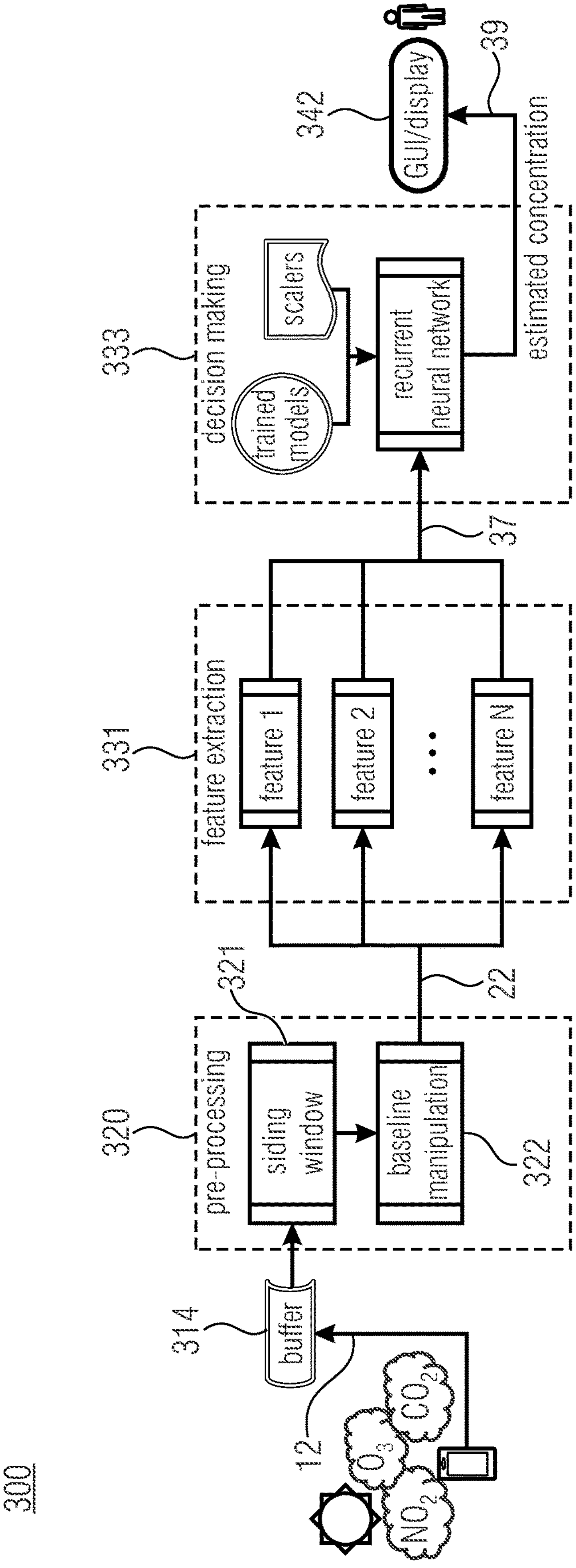
FIG. 3 illustrates a processing scheme for determining a sensing result according to an example.

FIG. 3 illustrates a processing scheme 300 for determining a sensing result according to an example. For example, the processing scheme 300 may be performed by the sensing device 2 as described with respect to FIG. 1 or FIG. 2. According to the example of FIG. 3, the gas sensing device comprises a buffer 314 for buffering the sampled measurement signal 12, and optionally also a corresponding temperature signal, which represents a temporal temperature profile to which the sensing units 64 are exposed by means of a heater, as described with respect to FIG. 2. In pre-processing block 320, the buffered sampled measurement signal 12 is, in block 312, segmented into overlapping or non-overlapping segments, e.g., by means of a sliding window. In other words, from the sequence of samples of the sampled measurement signal 12, a sub-sequence of samples, also referred to a segment of the sampled measurement signal, may be selected for further processing. The sub-sequence of samples may subsequently be subjected to a compensation 322, e.g., a baseline manipulation. For example, the compensation block 322 may correspond to the compensation module 20 as described before. For example, the segments of the sampled measurement signal 12 may be selected based on the temperature signal. For example, the length of the segments may correspond to one or multiple periods of the periodic temperature profile. For the baseline manipulation 322, a reference value, e.g., the sensor response to the synthetic air, as it may have been determined during a calibration procedure, may be used to normalize the sampled measurement signal to cancel sensor-to-sensor variations.

For example, the pre-processing block 320 may be performed by the compensation module 20. The compensated measurement signal 22 resulting from the baseline manipulation may be input to a feature extraction block 331. In the feature extraction block 331, the normalized sensor signals may be transformed and coded into features to represent a dynamic evaluation of the sensor response. Different types of features may be extracted, depending on the heater operating mode, e.g., the above-mentioned pulse mode or sine modes.

In other words, more generally speaking, the feature extraction block 331 may determine, based on the compensated measurement signal 22, a plurality of features, each of which represents a characteristic of the sample measurement signal 12, in particular, a characteristic of the currently considered segment of the sampled measurement signal 12. The entirety of features determined for a segment of the sampled measurement signal 12 are referred using reference sign 37.

For example, the features 37 may include time domain features representing characteristics of the sampled measurement signal 12 in the time domain, such as a normalized sensitivity, minima and maxima, and/or a derivation of the compensated measurement signal 22. Additionally or alternatively, the features 37 may include frequency domain features, which represent characteristics of the sampled measurement signal 12 in the frequency domain. To this end, the sampled measurement signal 12 may be transformed to the frequency domain, e.g., based on a frequency of the temperature profile of the heater.

The features 37 are input to a decision making block 333, which determines a sensing result 39. For example, the decision making block 333 may determine a decision on an air quality level, or may determine an estimation for respective concentrations of one or more target gasses of the gas sensing device 2. For determining the sensing result 39 based on the features 37, the decision making block 333 may use an algorithm, for example, a classification algorithm or a regression algorithm. For example, the algorithm may be a machine learning algorithm using a machine learning model, however, the present disclosure may be implemented independent of the choice of the algorithm.

For example, a model for the algorithm of the decision making block 333, such as an architecture of an artificial neural network and/or a set of parameters, are selected out of a pool of available trained models based on a current operating mode and optionally based on a used case. In other words, the algorithm of the decision making block may be, or comprise, an artificial neural network, which makes use of a model comprising a set of trained or learned parameters, e.g. weights, for the neural network, and a set of models may be available to the gas sensing device 2, which may select one of the models for the neural network based on a current operation mode.

Optionally, the sensing result 39 may be output for presentation to a user, e.g., using a display 342.

It is noted, that the processing scheme described with respect to FIG. 3 is exemplary. In particular, examples of the present disclosure do not necessarily make use of temperature profiles for heating the sensing units. Accordingly, the consideration of a temperature signal is optional, and in case that no temperature profiles are considered, the buffering of the sampled measurement signal and/or the segmenting using a sliding window may be omitted. Furthermore, it is noted that the feature extraction block 331 is optional, and the compensated measurement signal 12 may be (e.g., directly) subjected to an algorithm, e.g., an algorithm as described for the decision making block 333 to determine the sensing result 39, e.g., without determining features in advance.

For example, the feature extraction block 331 and/or the decision making block 333 may be performed by the processing module 30.

Accordingly, referring to the description of the gas sensing device 2 of FIG. 1, the processing module 30 may be configured for determining, for a sample of the compensated measurement signal 22, a set of features 37, the features representing respective characteristics of the compensated measurement signal 12, and determining a sensing result 39, e.g., a value for the concentration of the target gas, based on the set of features 37 using an algorithm, e.g., a machine learning algorithm (e.g., using a machine learning model), e.g. an artificial neural network (e.g. using a neural network model). For example, the characteristics represented by the features 37 may comprise the predetermined characteristic used for evaluating the first criterion.

For example, the compensation performed by the compensation module 20, and in particular, the baseline manipulation 322 of the preprocessing block 320 may represent the transformation of a sensor resistance into a relative resistance change with respect to the response to a reference analyte (the response to a reference analyte may be called baseline). For example, synthetic air may be used as a reference analyte as it is easily applicable and realistic in a real-world scenario. The purpose of using a baseline is to potentially create a more stable and reproducible sensor response by canceling the impact of the initial resistance values and removing some of the drift caused by gas exposure before the sensor was deployed in the field. Additionally, since the ohmic values of the raw resistance can occupy rather different value ranges (from a few hundred ohms to hundreds of kiloohms), the normalization step helps obtain variations that are more comparable, and the signals can then be sampled more effectively by the ASIC.

For example, the compensation by compensation module 20, and in particular, the baseline manipulation of block 322 may be performed as shown in Equation (1), i.e. by subtracting the sensor response R by its baseline $R_0$ removes additive drift, while division removes multiplicative drift. Using both operations results in the relative resistance change $\Delta R/R_0$:

$$\Delta R/R_0=(R-R_0)/R_0 \tag{1}$$

The relative resistance change will be addressed as sensitivity in this disclosure for simplicity.

In the following, exemplary drift behaviors of chemoresistive gas sensing units and the impact of the drift on concentration estimation are described to discuss the advantages of the present disclosure.

When first deployed in the field, a gas sensor may experience a warming-up phase, where the sensor resistance drifts downward as the sensor absorbs gas molecules in the environment and tries to reach an equilibrium, which typically happens after 1 to 2 weeks. Afterward, primarily due to the material oxidization caused by ozone (O3) molecules in the environment, the resistance consistently drifts upward in the long term. While the initial downward drift is limited to a couple of weeks and can be addressed during fabrication by improving for example the burn-in process in the front end, the upward drift has to be counteracted with appropriate techniques over the course of time.

As discussed before, detecting a sample, which is associated with a concentration of the target gas below the threshold allows for determining a time instance, which may be used for a reliable recalibration. Accordingly, changes of the sensing behavior of a sensing module may be accounted for without the need of changing an algorithm or a model, which may be used for determining the sensing result based on the measurement signal. Therefore, the disclosed concept allows to use, for the determination of the sensing result, an algorithmic model which is based on data from relatively short lab measurements, e.g., only a few days. Despite the fact that it is difficult to mitigate the effect of long-term drift with a lab calibrated model for the algorithm for mapping the raw signals to the estimations for the gas concentrations, and despite the fact that center drift may depend on specific environmental factors, and therefore may differ from location to location, the herein disclosed concept allows adapting this compensation of the measurement signal during operation, and may therefore account for long-term drifts and location specific behavior, even without external connectivity for updating a model for the algorithm. Accordingly, the herein disclosed concept may avoid or decrease a deviation of the estimated concentrations from the two values to start after a few weeks or months of operation in the field.

Figure 4:
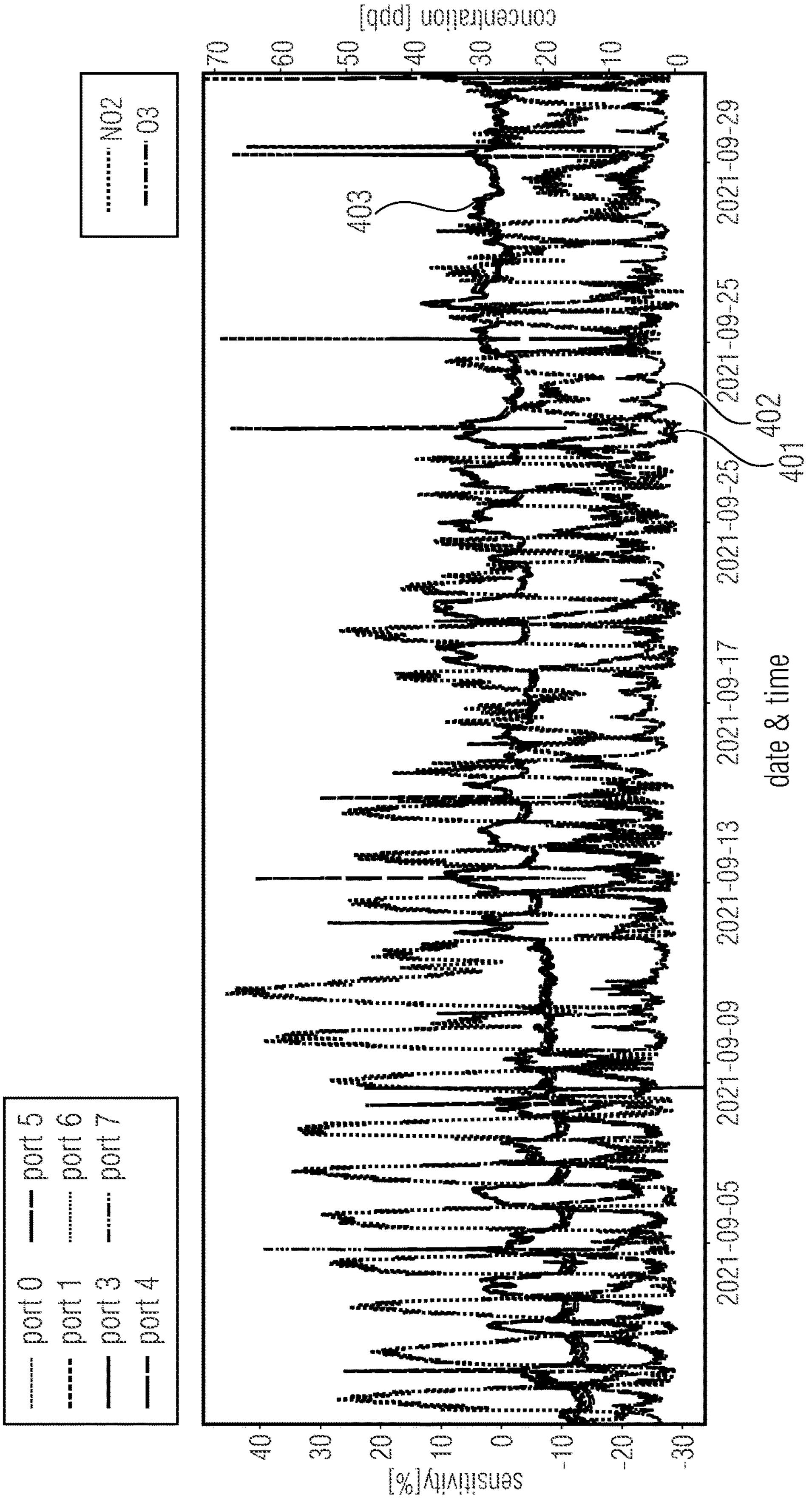
FIG. 4 shows an example of measured sensor sensitivities illustrating a sensor drift in pulse mode operation.

FIG. 4 shows a diagram with measurement data comparing the temporal evolution of the concentration of the gas $O_3$ (curve 401) and the gas $NO_2$ (curve 402) as obtained with a calibrated analyzer, with the sensitivity according to the above equation (1) of eight sensing devices, curves 403, operating, e.g., according to the scheme of FIG. 3 without the herein disclosed concept for updating the offset information being implemented. In particular, FIG. 4 illustrates the development of the relative resistance changes of the same sensing field in 8 different sensors when they were deployed in the field with the pulsed mode for over a month after the equilibrium is reached. The baseline was taken when the $O_3$ concentration had been extremely low (<3 ppb) for a few hours. As shown by FIG. 4, the sensor response to extremely low $O_3$ concentration (<3 ppb) and $NO_2$ concentration (<10 ppb) has increased by more than 10% within a month, although the lifespan of an electrochemical sensor is normally expected to be at least 3 years.

Figure 5:
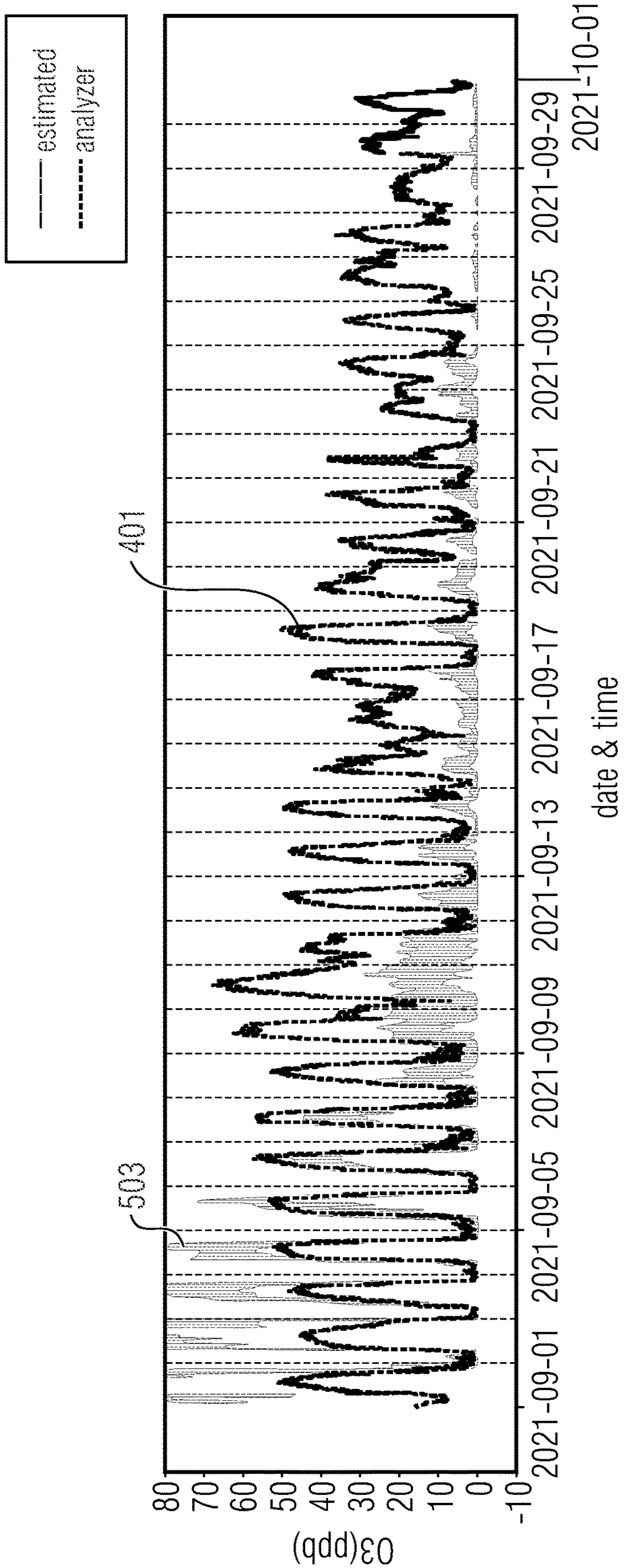
FIG. 5 shows an example of sensing results based on the sensor sensitivities of FIG. 4.

FIG. 5 shows another diagram comparing curve 401 of FIG. 4 with sensing results obtained from the compensated measurement signals 403 of FIG. 4 without recalibration of the baseline during operation. Without recalibration, the features extracted from the sensitivity can also be influenced by the upward drift. As shown in FIG. 5, after the baseline calibration, the estimated $O_3$ concentration was first slightly higher than the ground truth provided by the $O_3$ analyzer but then went lower and lower until finally becoming constantly around 0 ppb.

Figure 6:
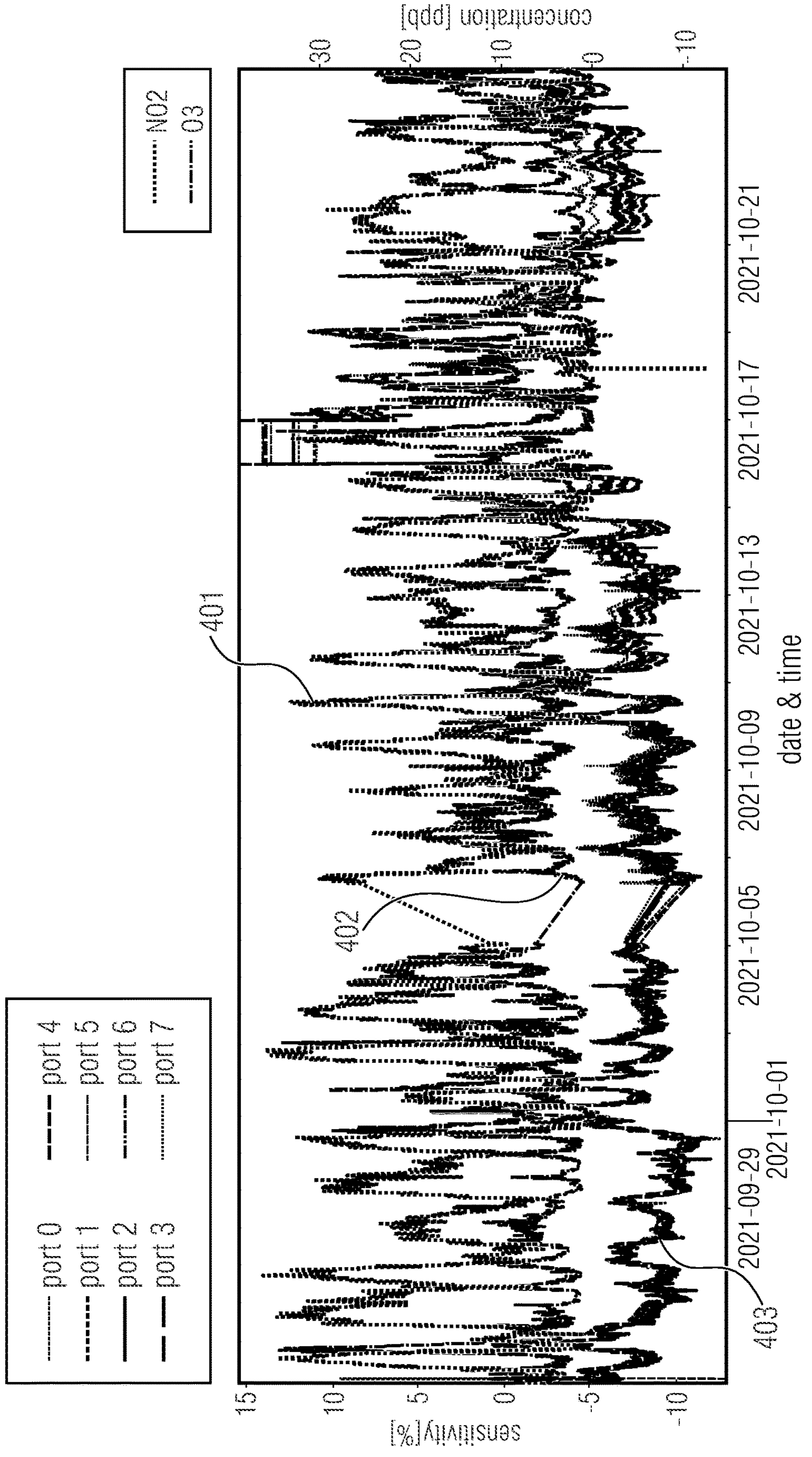
FIG. 6 shows an example of measured sensor sensitivities illustrating a sensor drift in sine mode operation.
Figure 7:
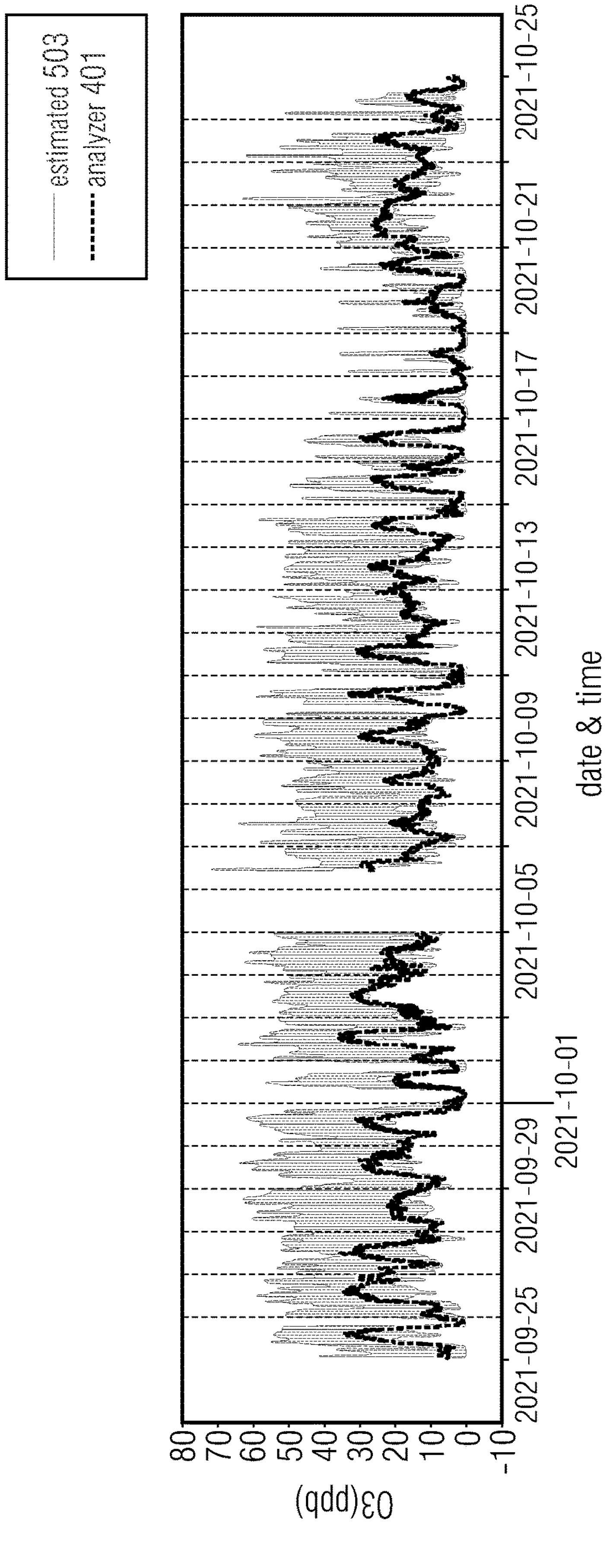
FIG. 7 shows an example of sensing results based on the sensor sensitivities of FIG. 6.

FIG. 6 and FIG. 7 show diagrams with measurement data similar to the diagrams of FIG. 4 and FIG. 5, respectively, but for a sine mode operation instead of a pulse mode operation. FIG. 5 illustrates the development of sensor sensitivities over a month of field deployment in sine mode, FIG. 6 illustrates $O_3$ estimates over a month without baseline recalibration in sine mode.

As already mentioned, besides time-domain features like sensitivities and derivatives, frequency-domain features may also be extracted for the sine-mode measurements to better exploit the waveform distortion introduced by the target gas(es). Although sine-mode may have a higher noise level, the frequency features tend to offer quicker responses to the environment changes compared to the sensitivities and are also more robust against baseline offsets. Consequently, the estimated $O_3$ concentration from the sine-mode data fluctuates in a wider range but remains stable throughout the whole month, as shown in FIG. 7. Even without any baseline recalibration, there is no obvious degradation of the model performance within a month.

Figure 8:
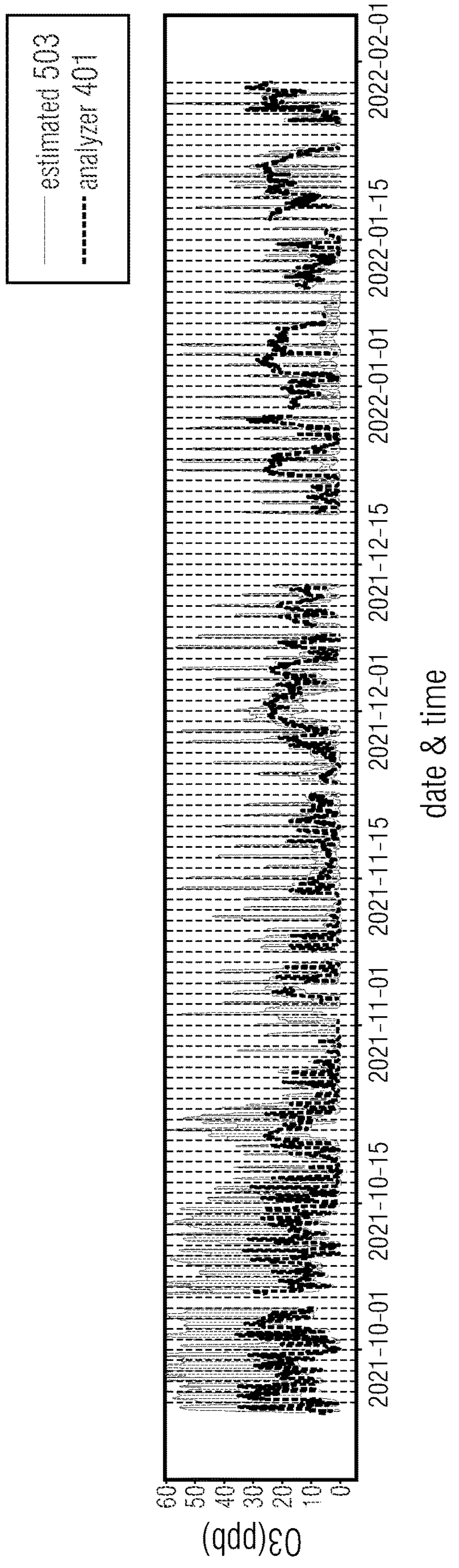
FIG. 8 shows another example of a drift of sensing results.

FIG. 8 illustrates a diagram with data similar to that of FIG. 7, but for a longer time period, namely for a month. Looking at the estimates of a longer period shown in FIG. 8, a similar effect as observed for the pulsed mode may appear: the estimated concentration decreases gradually over time and eventually became almost always zeros. The under-estimation first happens after the data loss at around December 15th, when the sensor response to extremely low $O_3$ and $NO_2$ concentrations had drifted over 20% upward.

This behavior may attributed to the fact that compared to the pulse mode, the sine mode may reduce the degradation of the sensor due to the $O_3$ exposure and the resulting oxidation but not entirely preventing degradation. As such, sooner or later, a drift of the baseline will be observed and will have to be compensated.

Accordingly, with both heater-operating modes (pulsed or sine), baseline recalibration may allow an achievement of good performance throughout the sensor lifetime. Alternatively, one could reduce the feature set to features intrinsically robust against drift, such as the phase angle of the fundamental frequency. However, baseline recalibration avoids such a reduction, which would imply a loss of information and would ultimately also impact the estimation accuracy. Also, the frequency domain features are the result of chemical processes happening at the surface of the sensors (chemisorption). Depending on the level of stress experienced by the sensor, these processes might become irreversible and distort the features-to-predictions mapping to a level that frequency domain features become obsolete and can no longer be used as input to the model trained in the lab 'at 0 hours'. At this point, in some cases only time domain features can be used to predict gas concentrations and baseline recalibration becomes a necessary step. The disclosed concept of updating the offset information allows using both time-domain and frequency-domain features in the long-run, such providing for a high accuracy over a long operation time.

It is noted that depending on the operating mode and extracted features, different algorithmic models could have different baseline tolerances. In the examples above, the pulse-mode model using only time-domain features may start to under-estimate immediately after an upward drift appears (o % drift tolerance), while the sine-mode model using both time- and frequency-domain features is more robust and can withstand, e.g., ~20% of upward baseline drift.

Examples of the present disclosure avoid the above-described problems by recalibrating the baseline so that the drift that happens after initial calibration is canceled in the compensated measurement signal, e.g., the sensitivity according to equation 1. However, the gas sensing device 2 may have no access to any reference device when operating in the field, at least not with a desired time and space granularity. The herein disclosed concept allows to pick a good calibration point, i.e., a time instance, where one or both of $O_3$ and $NO_2$ concentrations are expected or estimated to be low. The measurement signals obtained at such time instances may provide for a good approximation for recalibrating the baseline. The herein disclosed concept allows for avoiding periodic recalibration, e.g., in a lab, which is often expensive and time consuming, as it implies discontinuing the sensors for a few days or weeks until they can be placed again in the field. In contrast, the disclosed concept may allow for a recalibration during operation.

Figure 9:
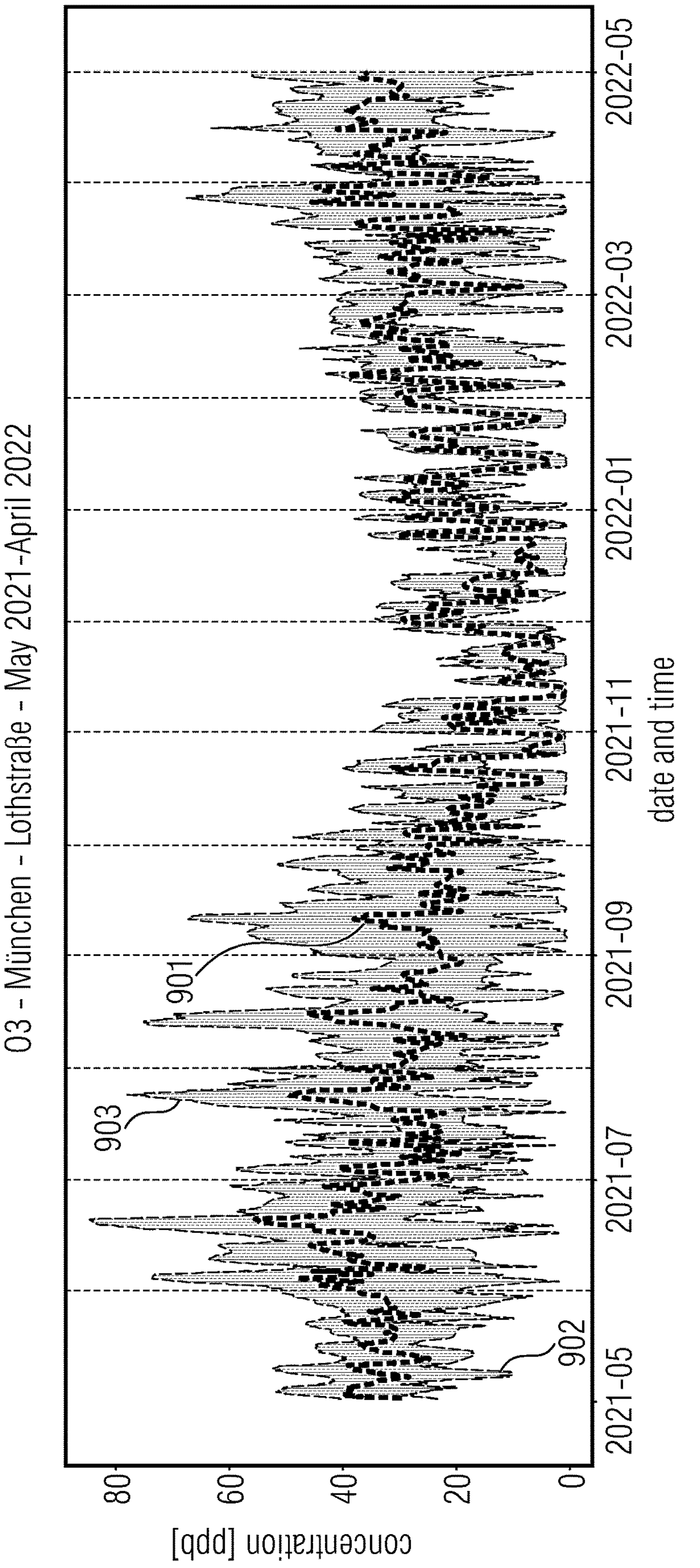
FIG. 9 illustrates an example of the O3 variation throughout the year.

FIG. 9 illustrates an example of the $O_3$ variation throughout the year in a typical urban background. As pointed out by the daily minima curve, an hourly average of extremely low $O_3$ concentration (<3 ppb) shows up almost every week, giving the sensor enough time to desorb gas molecules and to recover to a higher level of resistance. Considering the frequency of good recovery points in the field, automatic baseline recalibration is not only practical but also realistic. In FIG. 9, curve 901 represents the daily average, curve 902 the daily minima, and curve 903 the daily maxima.

Examples of the present disclosure rely on the finding that it is possible to locate appropriate recalibration points without ground truth, i.e., without a reference signal. As mentioned before, adsorbed gas molecules change the conductivity of multi-gas sensors. To be more specific, the sensor resistance value decreases as it absorbs ozone ($O_3$) or nitrogen dioxide ($NO_2$) in the environment and increases as the gas molecules are released back to the air. Therefore, when defining the baseline as the sensor response to synthetic air or the air with extremely low $O_3$ and $NO_2$ concentrations and use it for the normalization, it is expected that with adsorption the sensitivity becomes negative and with desorption the sensitivity would finally recover to 0%. Nevertheless, with the upward drift in the field, the sensitivity tends to increase over time and to finally land in the area above 0%, which corresponds to a smaller amount of target gas or no target gas in the lab measurements, thus the under-estimation. To make sure that the estimated concentration does not vanish over time, recalibrating the baseline to more up-to-date resistance values may bring the sensitivities back to negative.

In the following, several exemplary implementations for determining whether a sample associated with a concentration of the target gas is below the threshold are described.

Figure 10:
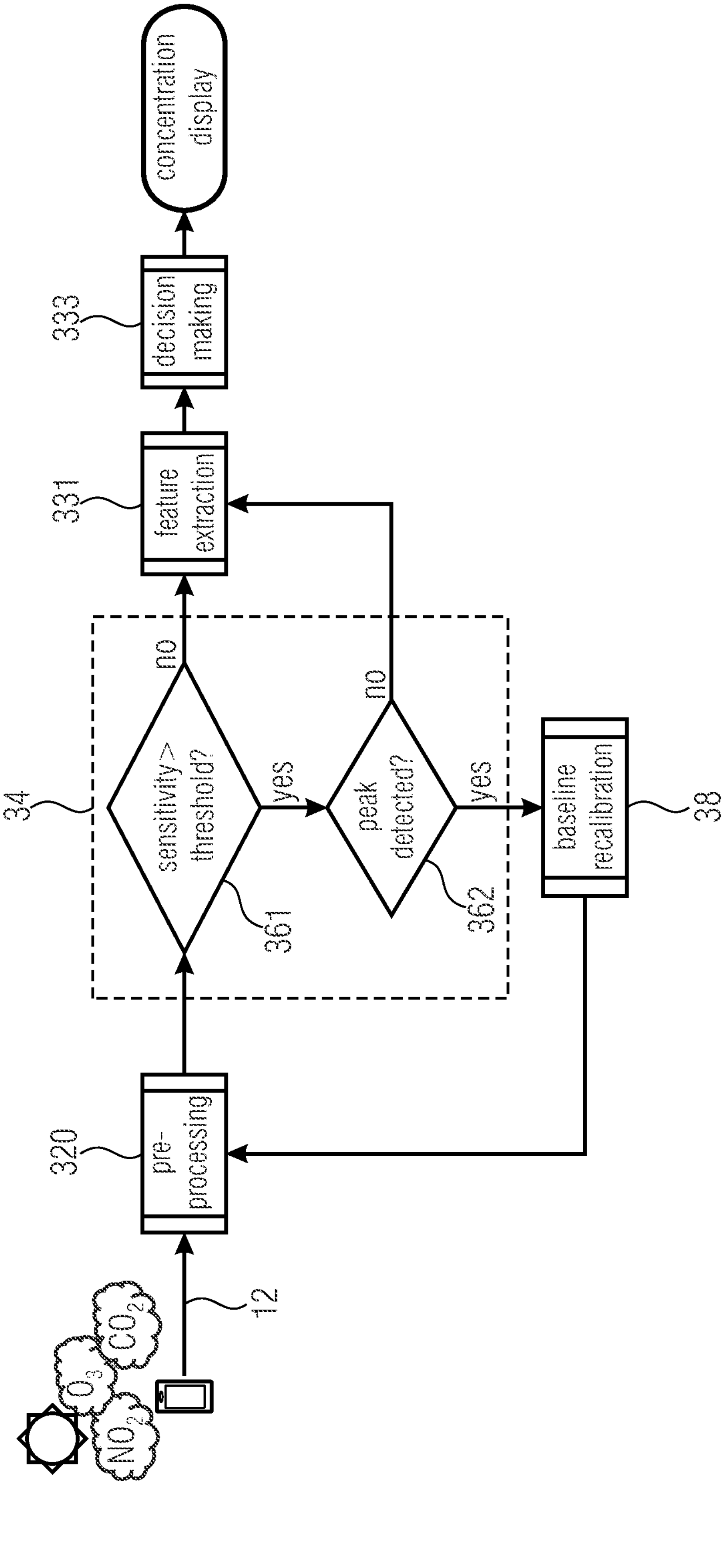
FIG. 10 illustrates an example of the detection block according to an example of the present disclosure, FIGS. 11 *a-c* illustrate data in different processing stages of an example of FIG. 10.

FIG. 10 illustrates an example of the detection block 34 according to an example of the present disclosure. In FIG. 10, the detection block 34 is exemplarily illustrated in the context of the scheme for determining a sensing result as described with respect to FIG. 3, however, as already mentioned with respect to FIG. 3, details of the processing scheme for determining the sensing result 39 are optional. According to the example of FIG. 10, the detection block 34 checks, in block 361, whether the sensitivity according to equation 1 is above a predetermined threshold. As apparent from equation (1), a sensitivity above a certain threshold, e.g., zero, may indicate that the concentration is below the threshold of the first criterion. In other words, the sensitivity may be an example of the characteristic with respect to which the compensated measurement signal 22 may be evaluated for detecting whether a sample is associated with a concentration below the predetermined threshold. If the sensitivity is above the threshold, which may be zero in the example of the sensitivity according to equation 1, the currently considered sample may be considered for performing a baseline recalibration, or more generally speaking, for updating the offset information 24.

Accordingly, the detection block 34 may compare a sample of the compensated measurement signal 22, in particular compensated measurement values of the sample, with a threshold in order to check, whether the sample fulfils the predetermined criterion.

In order to reduce the frequency with which the offset information 24 is updated, the detection block 34 may optionally comprise a further step of a peak detection 362. To this end, the detection block 34 may check whether the currently considered sample represents, with respect to the predetermined characteristic, a local extremum in the sequence of samples of the compensated measurement signal 22. For example, in case that the checking for the first criterion involves a check whether a value assumed by the predetermined characteristic is above a threshold, e.g., in the just described case of the sensitivity, the peak detection may search for local maxima while, if the check for the first criterion involves a check whether a value assumed by the predetermined characteristic is below a threshold, the peak detection may involve a search for a local minimum. Implementing the peak detection may avoid a repeated updating of the offset information 24 for subsequent samples. If the peak detection detects a local extremal, the currently considered sample may be used for the updating 38 of the offset information 24, otherwise the processing module 30 may proceed with determining a sensing result and/or with checking the set of criteria for a subsequent sample.

In other words, according to examples, the set of criteria comprises a second criterion, which is fulfilled if the sample represents an extremum, e.g., a local extremum, of the compensated measurement signal 22 with respect to the predetermined characteristic. For example, the second criterion is not fulfilled if the sample does not represent an extremum, e.g., a local extremum, of the compensated measurement signal 22 with respect to the predetermined characteristic.

For example, the extremum may be a local extremum, e.g. an extremum within a segment of a sequence of segments of the sampled measurement signal. Alternatively, the extremum may be defined by a predetermined prominence, e.g. a predetermined height over neighboring samples.

It is noted that the peak detection may be either performed on the compensated measurement signal 22 or on the sampled measurement signal 12.

In other words, a peak detection algorithm may be applied to the raw signals, or the compensated signals, to identify the best recovery point the sensor achieves within a certain period. For example, the best recovery point may refer to the sample, for which the predetermined threshold is exceeded the most among samples within the certain period.

The combination of a threshold and a peak detection allows for a reliable recalibration of the base line at comparably low effort. In particular, a local maximum alone does not necessarily guarantee that the gas concentration at the detected maximum is as low as being suitable for recalibration, e.g., below 3 ppb for $O_3$. The combination with the threshold may filter out the candidates for recalibration. For example, in case of the pulse mode, the threshold against which the sensitivity is tested may be 0%.

For example, for the peak detection, a max function may be used to individual signal segments above the 0% threshold of the sensitivity to extract the local maxima from the pulsed mode measurement data as candidates for possible recalibration points. In general, also other methods for peak detection are possible.

Figure 11A:
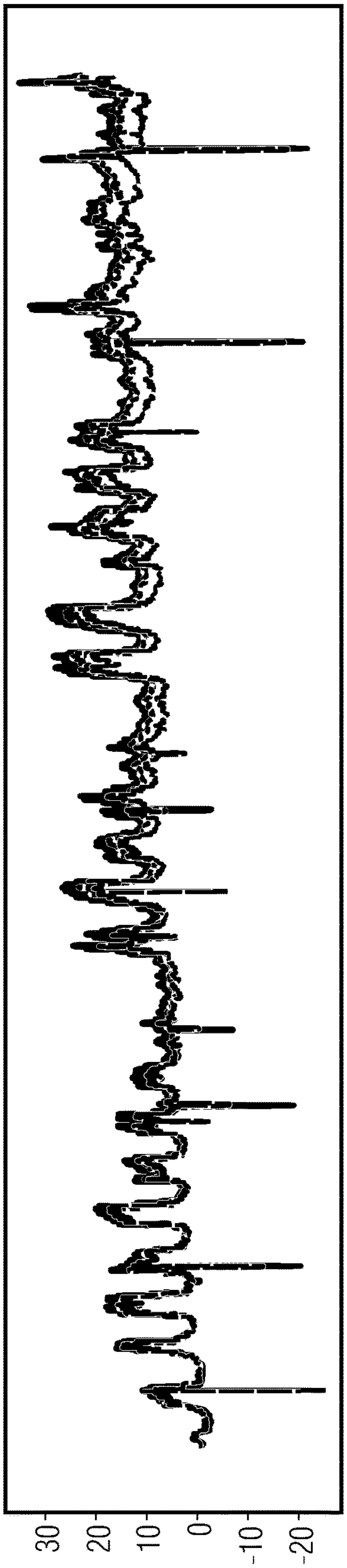
Figure 11B:
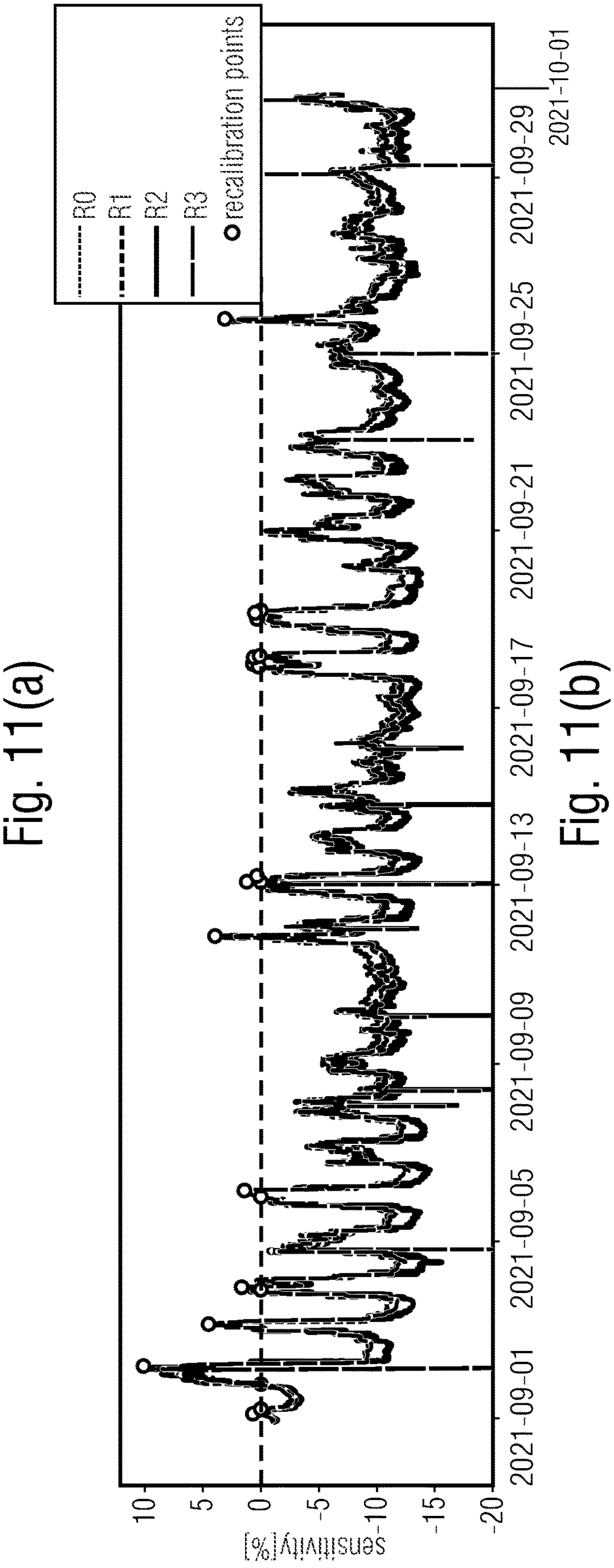
Figure 11C:
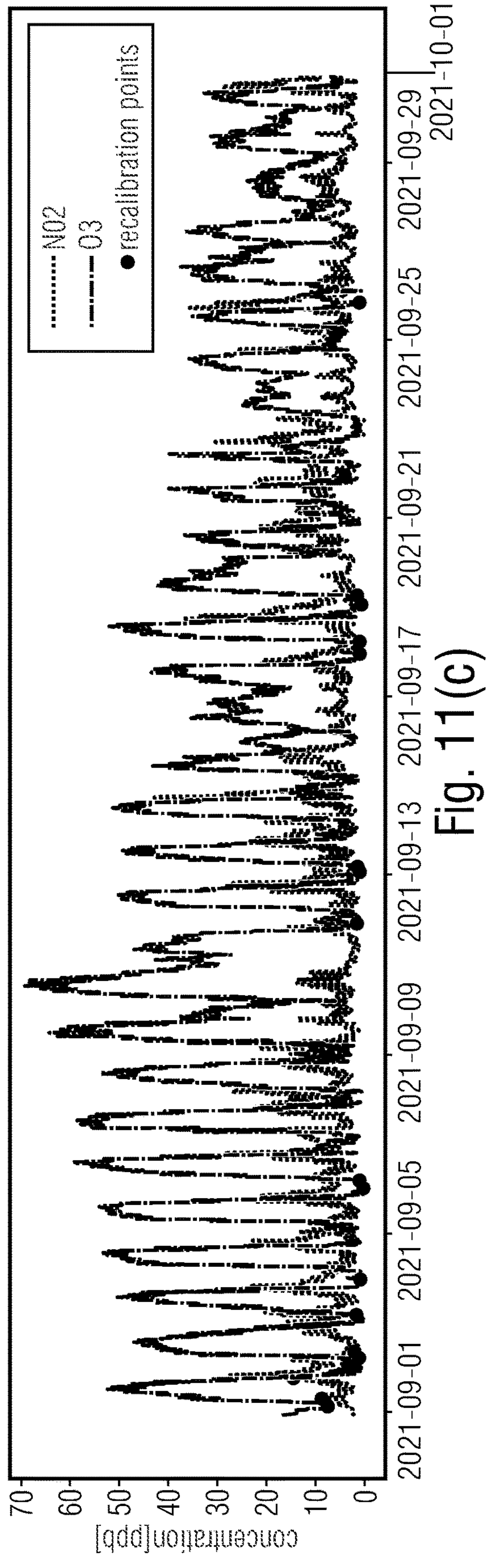

FIG. 11, comprising panels (a) to (c), illustrates the scheme of FIG. 1 by means of exemplary data. Subplot (a) illustrates the sensitivity features of a sensor array calculated with a suboptimal baseline, which is the peak of the data on September $1^{st}$ without baseline recalibration. Meanwhile, in subplot (b), the baseline is continuously updated throughout the measuring period and the recalibration points are marked as bullets. Every time the sensitivity value crosses the 0% threshold and becomes positive, the max value of the sensor resistance from that moment on would be kept in memory. When the signal returns to negative again, the baseline value would be updated and applied to the upcoming samples. If computation resource allows, one can use the max value of a moving average of the resistance as the new baseline to improve the robustness against noise. As apparent from FIG. 11(*b*), being efficient with both memory and computational resource, this method is also robust against the noise/spikes in field measurements. When marking the recalibration points also with the ground truth, as shown in FIG. 11(*c*), it is demonstrated that these locations correspond to extremely low $O_3$ and $NO_2$ concentrations, if not 0 ppb of both of them.

It is noted that even with the 0% threshold peaks can be detected where the concentrations are relatively high, such as the first point detected on September 5th in FIG. 11. However, by triggering recalibrations at such moments, the baseline is at least increased to a certain extent and the upward drift is at least partially removed. Whenever a better recalibration point shows up, the resistance would reach a new high and the sensitivity would then become positive, which guarantees another recalibration.

As illustrated in FIG. 11, features may then be extracted with sensitivities calculated with the constantly updated baseline and fed to the neural network.

Figure 12:
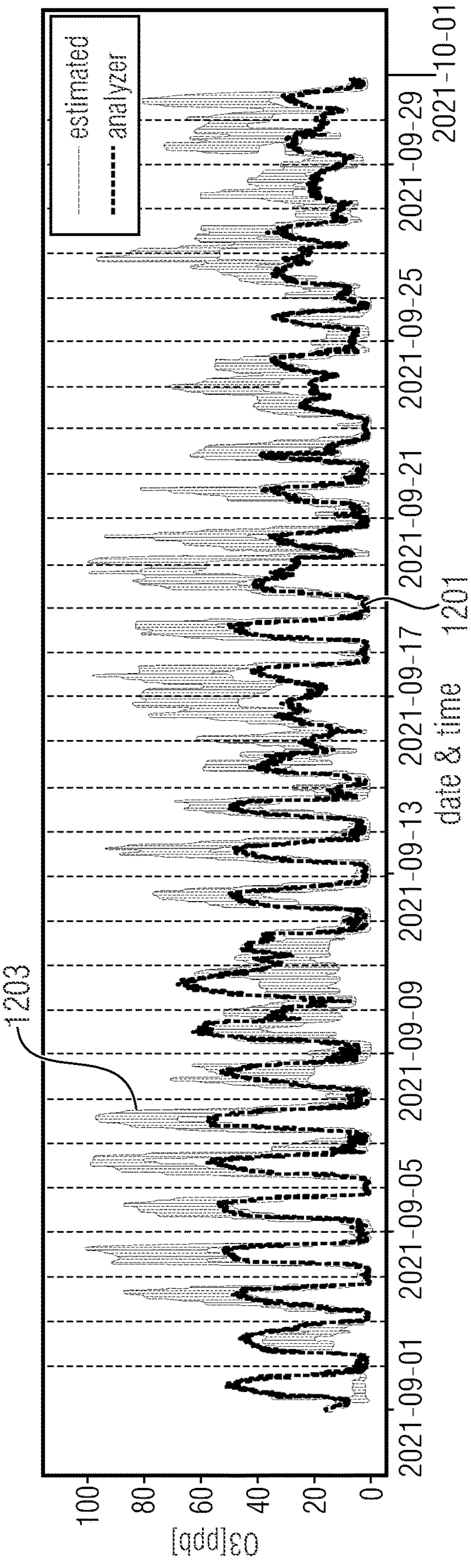
FIG. 12 illustrates sensing results obtained with updating the offset information according to an example.

FIG. 12 depicts a comparison between the resulting $O_3$ estimates, curve 1203, with the ground truth, curve 1201. Despite the under-estimation on September $1^{st}$ caused by a suboptimal initial baseline, the accuracy quickly improves and the estimation remains stable throughout the whole measurement period with only slight over-estimation.

It is noted that the drift tolerance may depend on the operating mode and the feature selection. Accordingly, the threshold for the sensitivity may be adjustable dependent on the application. For example, for $O_3$ detection with the sine mode, a threshold of 20% sensitivity can be applied to reduce computational efforts.

Further, it is noted that the peak detection may be implemented independent of the choice of the predetermined characteristic. In other words, the peak detection may also be applied in combination with other choices for the predetermined characteristic.

A further example for the predetermined characteristic is a total harmonic distortion, THD, which is a measurement of the harmonic distortion present in a signal, for example, the ratio of the sum of the powers of all harmonic components to the power of the fundamental frequency. Here, the fundamental frequency may refer to a frequency of the temperature profile applied to the sensing units 64. In other words, the predetermined characteristic may be a frequency domain feature extracted from measurement signals in sine mode, i.e., derived in combination with a sinusoidal temperature profile. As already mentioned, multiple frequency domain features could be extracted from the sine mode signals to improve the robustness of the concentration estimation algorithm, e.g., as implemented by the decision making block 333. Accordingly, the predetermined feature may be part of the set of features 37. In case of the total harmonic distortion (THD), low values of the THD may be associated with a low concentration of the target gas. Accordingly, in case of THD, the peak detection may detect, instead of peaks, minima. Similarly, in the scheme of FIG. 10, the detection block 34 may check, in block 361, whether the THD associated with the currently considered sample is below a predetermined threshold, and consider the respective sample for updating the offset information, if the THD is below the predetermined threshold (optionally in dependence on whether a local minimum is detected, cf. description of block 362).

Figure 13A:
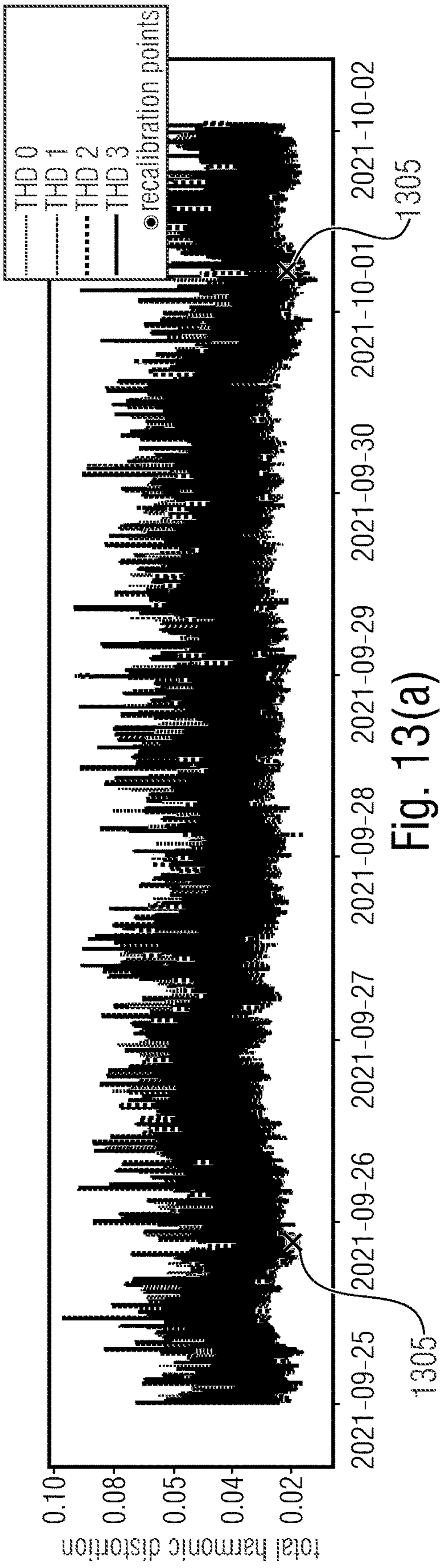
FIGS. 13*a-b* illustrate data for the total harmonic distortion (THD) according to an example.
Figure 13B:
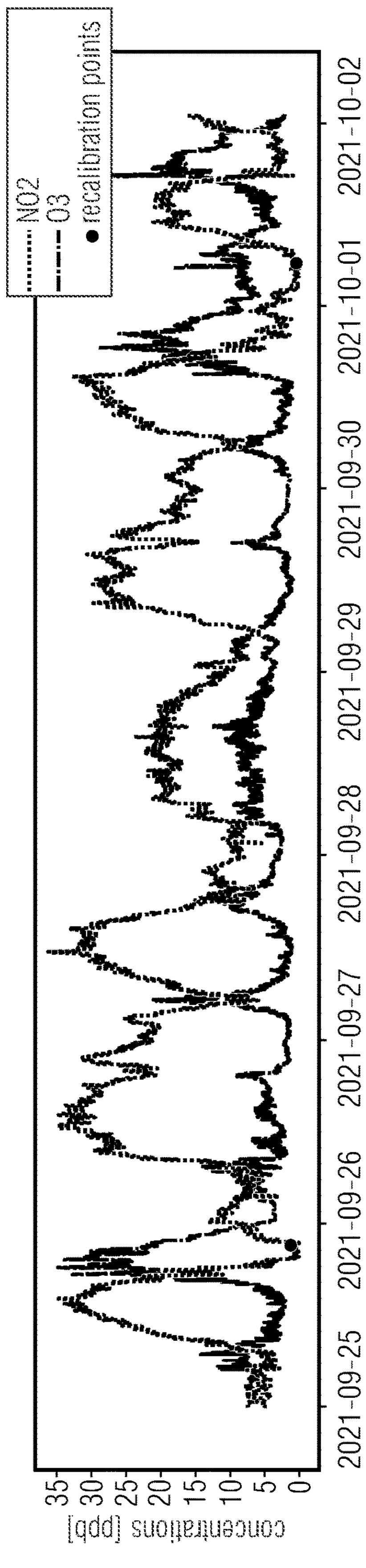

FIG. 13, comprising panels (a) and (b), illustrates an example of how valleys of the THD may be used as recalibration points. The data shown in FIG. 3 represents a period of one week. Subplot A of FIG. 13 shows detected values in the THD features. Subplot B illustrates corresponding gas concentrations of the recalibration points. As it is apparent from FIG. 13, the detected valleys 1305 match two final moments of a few hours of low 03 concentrations, where the sensor had the best possible recovery. Despite the upward drift in the sensor signals, the THD remained at the same level.

It is noted that even if frequency domain features, such as THD, may age over time and, therefore, are possibly not suitable as input to a prediction model, e.g., as implemented by detection making block 333, the frequency domain features may still remain immune to drift, and may therefore be used for locating the baseline as an alternative or in combination with the sensitivity.

More generally, according to examples of the present disclosure, the measurement model 20 comprises, or is connected with, at least one chemo-resistive gas sensing unit for sensing the target gas, and the measurement module 20 is configured for obtaining the sample measurement signal 12 using the chemo resistive gas sensing unit. According to this example, the measurement module 20 further comprises means for heating the chemo resistive gas sensing unit according to a periodic temperature profile. For example, the means for heating may be a heater arrangement or a heater, e.g., a thermal heater. According to this example, the characteristic, e.g., the predetermined characteristic, is a frequency domain characteristic, and the processing module 30 is configured for performing the evaluation of the sampled measurement signal 22 on a sequence of samples of the compensated measurement signal 22 with respect to the frequency domain characteristic, e.g., the THD.

Accordingly, additionally or alternatively to the sensor resistance itself, for the sine-mode measurements, frequency-domain features such as THD may be used to locate the baseline recalibration points and thus to improve the effectiveness of the sensitivities. Compared to the time-domain features, THDs may be noisier but much more robust against the baseline drift, making them more reliable in the long run where there could be interruptions in the measurement.

It is noted that as described before, the sensing unit 64 may alternatively be external to the measurement module 20, i.e., the measurement module 20 may be configured for receiving the sampled measurement signal 12 and a temperature signal representing the periodic temperature profile from a chemo resistive gas sensing unit for sensing the target gas, the chemo resistive gas sensing unit comprising the means for heating.

According to examples of the processing module 30 of FIG. 1, and optionally according to any of the implementations described with respect to FIG. 2, FIG. 3, or FIG. 10, the processing module 30 may be further configured for determining a temporal model for the offset information 24 based on a plurality of detected samples which fulfil the set of criterions, e.g. samples of the sampled measurement signal 12 or samples of the compensated measurement signal 22. For example, the temporal model may be a model for a future change of the offset information 24. According to this example, the processing module 30 may update the offset information 24 based on the temporal model.

In other words, the peak detection algorithm can be strengthened with an adaptive drift model, which may be fitted to the latest peaks detected in the raw signals and can be used to correct baseline values constantly before the next peak shows up.

For example, the temporal model may comprise a polynomial function, and the processing model 30 may determine the temporal model by determining parameters for the polynomial function based on the plurality of detected samples, which fulfil the set of criterions.

For example, optionally, the peak detection algorithm described with respect to FIG. 10 may be complimented with an adaptive drift model, which is time dependent and fitted to the peaks detected in a certain period of time, for example, within the past four weeks. For example, a first order polynomial may be used for the drift model to constantly correct the base line used in preprocessing even when a peak is not yet detected.

For example, the processing module 30 may determine the temporal model by detecting, for each of a plurality of segments, e.g. sequential segments or subsequent segments, of the sampled measurement signal 12 or the compensated measurement signal 22, a respective extremum with respect to the predetermined criterion, to obtain a sequence of extrema. The processing module may fit the temporal model to the sequence of extrema to obtain parameters for the model.

Figure 14:
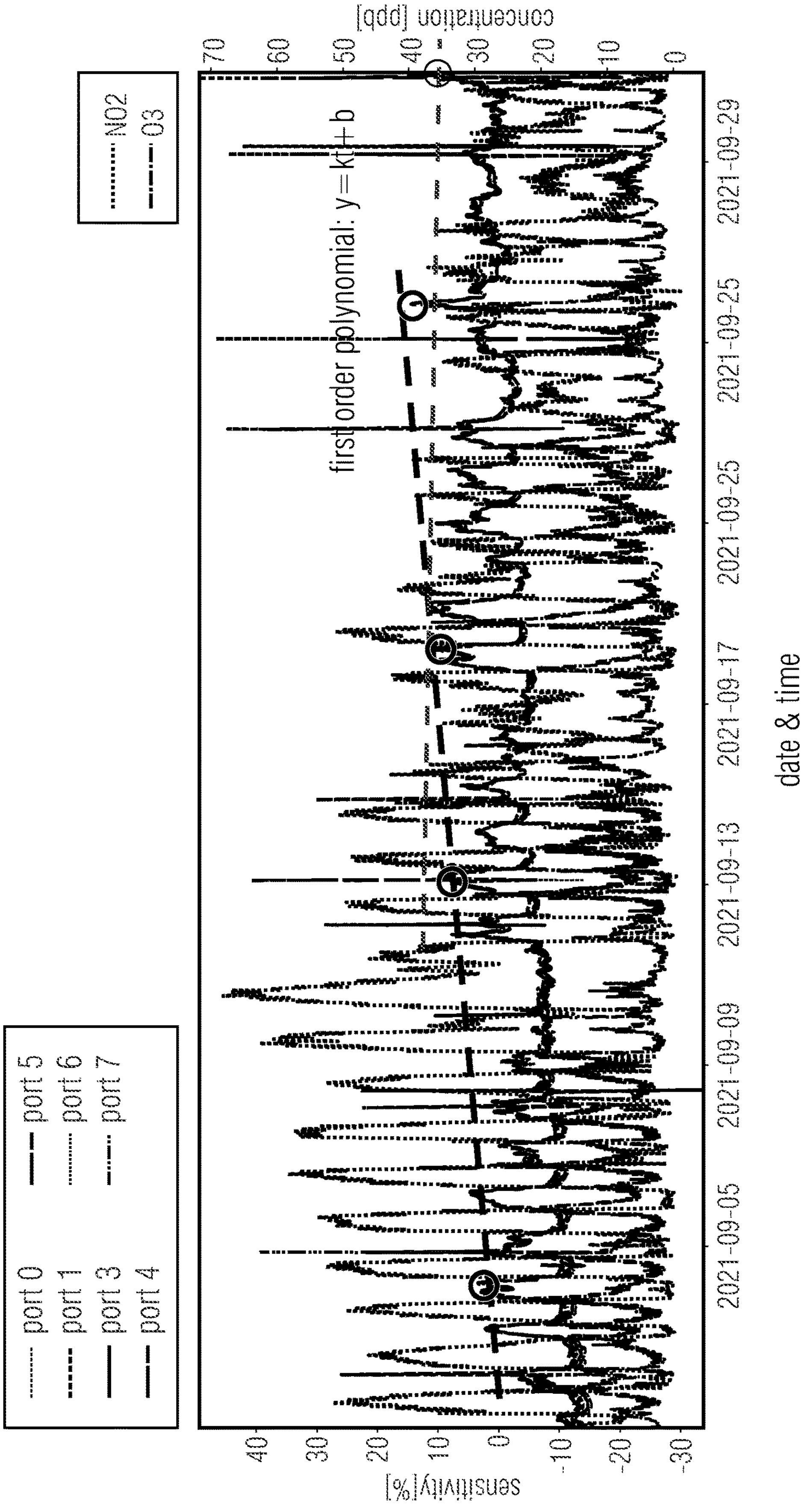
FIG. 14 illustrates an example of a drift model.

FIG. 14 illustrates an example of a first-order polynomial drift model fitted to the resistance weekly peaks in the past 4 weeks. When a new week is finished, the model may be adjusted with the latest weekly peak replacing the oldest one, and the adapted model is then used for the calculation of the baseline used in the upcoming week. For each data sample, instead of taking the baseline calibrated at the last extrema, an adjusted baseline may be calculated using the drift model and the corresponding time stamp.

Figure 15:
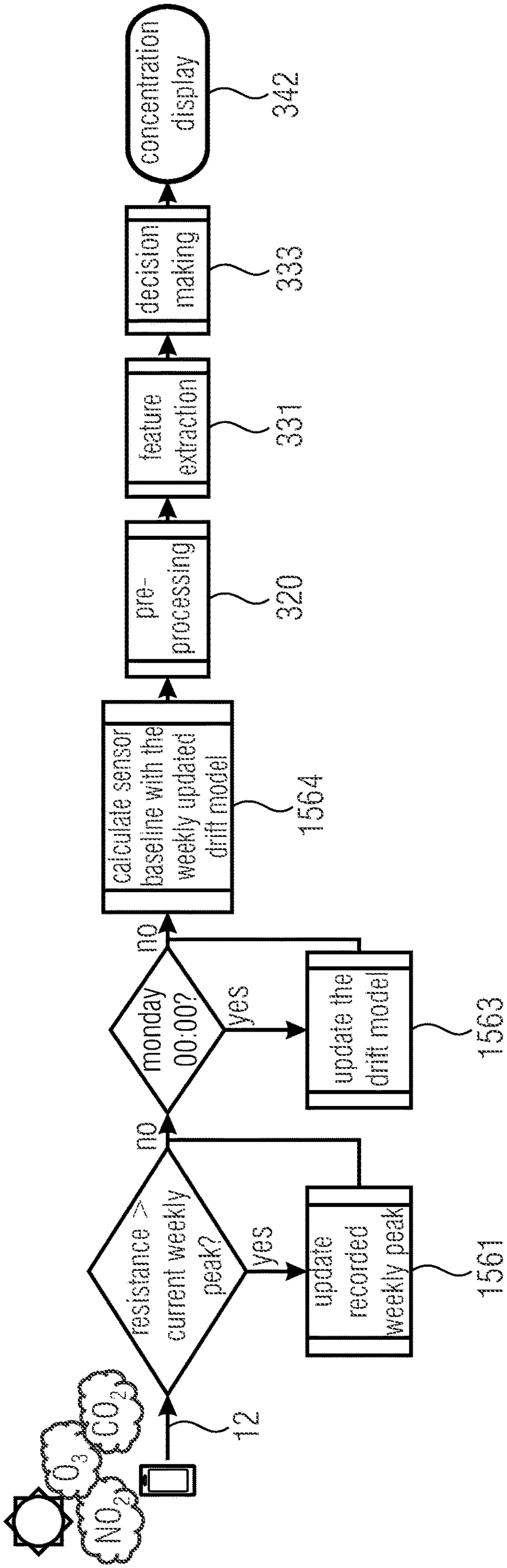
FIG. 15 illustrates a processing scheme for a drift model according to an example.

FIG. 15 illustrates a processing scheme implementing a drift model according to an example of the present disclosure. According to the example of FIG. 15, in block 1561, a maximum in the resistance of a sensing unit for a predetermined time period, such as one week, is detected by checking, for each of the samples of the sampled measurement signal 12, whether a resistance value of the sample is larger than a current maximum value for the predetermined time period and, if so, the current maximum value dated using the resistance value of the currently considered sample. After the predetermined time period has expired, the maximum value for the predetermined time period is used for updating 1563 a drift model. That is, for example, the maximum value is added to the drift model, e.g., for replacing an old maximum value. In block 1563 a drift model may be determined based on a predetermined number of maximum values of a predetermined number of previous time periods. The drift model updated in block 1563 may be used in block 1564 for recalculating the offset information, e.g. the sensor baseline.

In other words, as shown in FIG. 15, while an update of the maximum resistance value in block 1561 is possible for each new data sample, an adaption of the drift model in block 1563 is treated less frequently, for example once a week. Compared to the scheme of FIG. 10, the processing scheme of FIG. 15 may be more flexible, while the scheme of FIG. 10 may require less computational power.

In other words, according to an example, the processing module 30 may perform the evaluation of the sampled measurement signal 20, based on which the sample detection 34 is performed, by evaluating the sampled measurement signal 12 regarding the values of the samples of the sampled measurement signal 12, wherein the threshold for the first criterion is an adaptive threshold which depends on previous samples of a segment of segments of the sampled measurement signal 12, to which segment the currently evaluated sample belongs. According to this example, for each of the segments, a sample representing the lowest concentration among samples of the segment, may be detected, and the sequence of detected samples for a sequence of segments may be used for determining the temporal model. As illustrated in FIG. 15, the adaption of the threshold may be based on a measurement value of a sample, which fulfills the first criterion.

It is noted that the drift model may be determined based on the raw sensor signals 12, e.g. as illustrated in FIG. 15, or, alternatively based on the compensated measurement signal 22.

Figure 16:
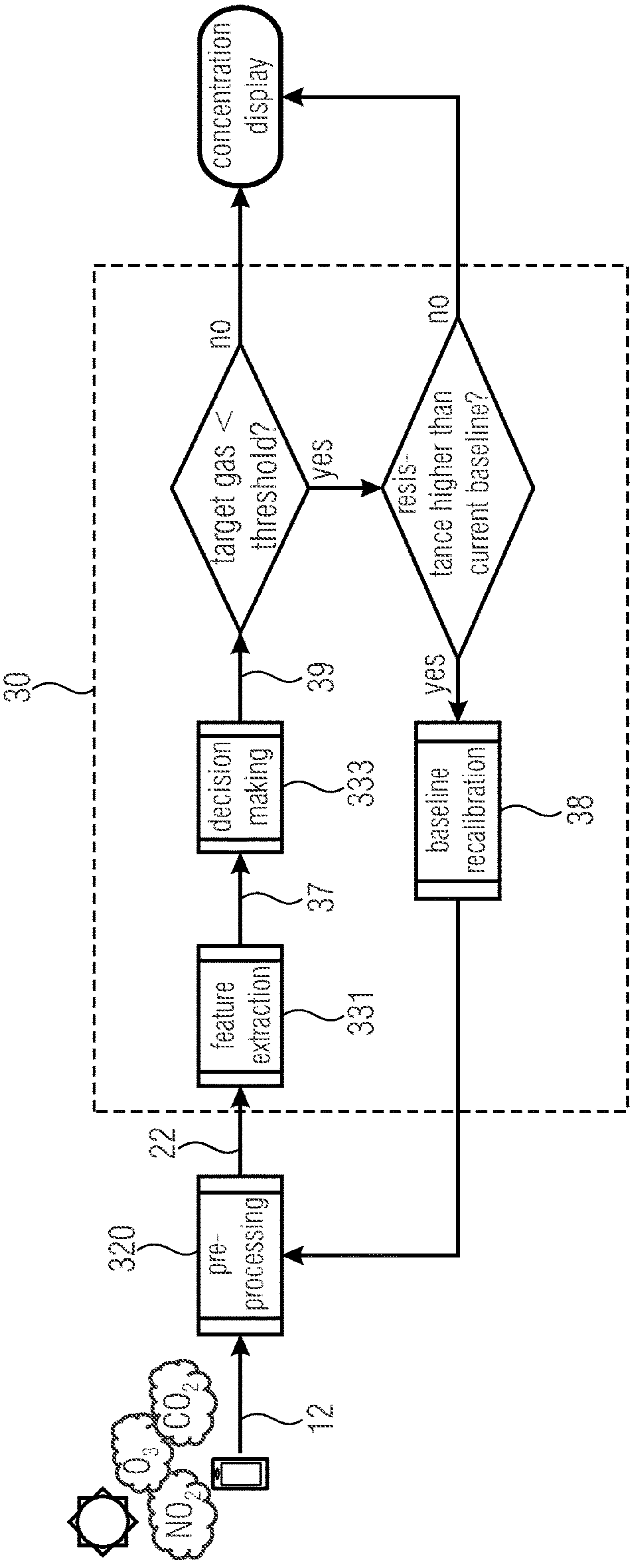
FIG. 16 illustrates a processing scheme for the detection block according to another example of the present disclosure.

FIG. 16 illustrates a processing scheme for the gas sensing device 2 according to another example of the present disclosure. According to the example of FIG. 16, the processing module 30 is configured for performing the evaluation of the sampled measurement signal 22 by using an algorithm to determine a sensing result 39. According to this example, the first criterion is fulfilled if the sensing result indicates that the concentration of the target gas is below the threshold.

In other words, according to the example of FIG. 16, the sensing result 39 obtained using the algorithm is for checking whether or not the sample is associated with a concentration of the target gas below the threshold. In FIG. 16, the algorithm is represented by the decision making block 333 as described with respect to FIG. 10, which determines the sensing result 39 based on the features 37 provided by the feature extraction block 331. However, as described with respect to FIG. 10, the separation of features extraction 331 and decision making 333 is optional and, in other examples, the compensated measurement signal 22 may, directly, by input to the algorithm. As described with respect to FIG. 10, the algorithm may rely on an algorithmic model, such as a machine learning model.

Optionally, in the example of FIG. 16, in particular in examples in which the sampled measurement signal 12 represents a resistance or a conductance of a chemo resistive sensing gas sensing unit, the set of criteria comprises a second criterion, which is fulfilled if a value of the sample of the sampled measurement signal 12 indicates that the resistance of the chemo resistive gas sensing unit is above a further threshold. For example, the further threshold may correspond to a current value of the base line, i.e., the offset value of the offset information 24.

With respect to FIG. 16 it is further noted that the preprocessing block 320 may correspond to the function of the compensation module 20 and may optionally be implemented as described with respect to FIG. 10.

In other words, according to an alternative example of the present disclosure, the base line may be recalibrated when the estimated gas concentration is below a certain threshold, such as 3 ppb. As the upward drift might result in underestimation, as described before, the actual concentration could be higher than the threshold. Therefore, an additional check could be applied to ensure the new baseline is at least higher than the existing one. Therefore, according to an example, the base line may be recalibrated when the estimated gas concentration is below a certain threshold, e.g., 3 ppb, and the resistance is higher than the current baseline, e.g., as shown in FIG. 16. Such an implementation may be particularly beneficial in cases in which the computational resource is limited on the target hardware platform.

The combination of the first and the second criterion, as described with respect to FIG. 16, relies on the finding that an up-wards drift often results in underestimation and that the first criterion could even be fulfilled when the actual concentration is higher than the threshold, although the estimation of the gas concentration indicates a concentration below the threshold. With the additional second criterion referring to the resistance value, this ensures that only resistances higher than the current baseline are taken as new baseline values. Similar to the recalibration points chosen by the extrema detection algorithm, even when the concentration is not low enough, the under-estimation is reduced to a certain extent. Different from examples of the extrema detection algorithm, the recalibration may be continuously triggered as soon as the resistance passes the original baseline and only stops when the highest value is reached. Although the highest resistance often indicates the best recovery in the neighborhood, it could also be noise or a spike, making this approach slightly less robust when the signal quality is not good enough. This could be the case in the presence of ageing of the sensor and as such, the proposed example could be particularly beneficial in the early lifetime of the sensor when raw data is usually cleaner and more reproducible.

In other words, examples of this disclosure propose a method to alleviate the impact of the sensor drift on the estimated concentration by calibrating the sensor baseline automatically with an extrema detection algorithm applied to selected features, or alternatively with a threshold comparison of the output feedback and of the extracted resistance feature, in both cases without the need for the connectivity to any reference device and with extremely low usage of computational resources.

The disclosed automatic baseline correction algorithm, e.g., the one based on the extrema detection algorithm, but also the one based on the threshold, applied to the extracted features allows maintaining a good performance of the chemo resistive gas sensors throughout a lifetime and, at the same time, the algorithm is efficient with respect to computational cost and memory footprint. The algorithm may optionally be complimented with an adaptive drift model, as described with respect to FIG. 15, in particular, when there is extra computing power available. The adaptive drift model provides improved flexibility. In particular, in cases of limited computational resources, the extrema detection may be replaced with a feedback loop from the output of the algorithm, e.g., the neural network, with a relatively small sacrifice instability. In particular, the proposed algorithms may improve long term performance and robustness without additional connectivity requirements.

Although some aspects have been described as features in the context of an apparatus it is clear that such a description may also be regarded as a description of corresponding features of a method. Although some aspects have been described as features in the context of a method, it is clear that such a description may also be regarded as a description of corresponding features concerning the functionality of an apparatus.

Some or all of the method steps may be executed by (or using) a hardware apparatus, like for example, a microprocessor, a programmable computer or an electronic circuit. In some examples, at least some of the method steps may be executed by such an apparatus.

Depending on certain implementation requirements, examples of the disclosure can be implemented in hardware or in software or at least partially in hardware or at least partially in software. The implementation can be performed using a digital storage medium, for example a floppy disk, a digital video disc (DVD), a Blu-Ray, a compact disc (CD), a read-only memory (ROM), a programmable read-only memory (PROM), an erasable programmable read-only memory (EPROM), an electrically erasable programmable read-only memory (EEPROM) or a Flash memory, having electronically readable control signals stored thereon, which cooperate (or are capable of cooperating) with a programmable computer system such that the respective method is performed. Therefore, the digital storage medium may be computer readable.

Some example embodiments according to the disclosure comprise a data carrier having electronically readable control signals, which are capable of cooperating with a programmable computer system, such that at least some of the methods described herein is performed.

Generally, example embodiments of the present disclosure can be implemented as a computer program product with a program code, the program code being operative for performing one of the methods when the computer program product runs on a computer. The program code may for example be stored on a machine readable carrier.

Other example embodiments comprise the computer program for performing at least some of the methods described herein, stored on a machine readable carrier.

In other words, an example embodiments of the inventive method is, therefore, a computer program having a program code for performing one of the methods described herein, when the computer program runs on a computer.

A further example embodiment is a data carrier (or a digital storage medium, or a computer-readable medium) comprising, recorded thereon, the computer program for performing at least some of the methods described herein. The data carrier, the digital storage medium or the recorded medium are typically tangible and/or non-transitory.

A further example embodiment is a data stream or a sequence of signals representing the computer program for performing at least some of the methods described herein. The data stream or the sequence of signals may for example be configured to be transferred via a data communication connection, for example via the Internet.

A further example embodiment comprises a processing means, for example a computer, or a programmable logic device, configured to or adapted to perform at least some of the methods described herein.

A further example embodiment comprises a computer having installed thereon the computer program for performing at least some of the methods described herein.

A further example embodiment according to the disclosure comprises an apparatus or a system configured to transfer (for example, electronically or optically) a computer program for performing at least some of the methods described herein to a receiver. The receiver may, for example, be a computer, a mobile device, a memory device or the like. The apparatus or system may, for example, comprise a file server for transferring the computer program to the receiver.

In some example embodiment, a programmable logic device (for example a field programmable gate array) may be used to perform some or all of the functionalities of the methods described herein. In some examples, a field programmable gate array may cooperate with a microprocessor in order to perform at least some of the methods described herein.

The apparatus described herein may be implemented using a hardware apparatus, or using a computer, or using a combination of a hardware apparatus and a computer or other combinations of elements.

The methods described herein may be performed using a hardware apparatus, or using a computer, or using a combination of a hardware apparatus and a computer or other combinations of elements.

In the foregoing Detailed Description, it can be seen that various features are grouped together in exemplary embodiments. It is noted that subject matter of the disclosure may be present in less than all features of a single disclosed embodiment. It is also noted that the disclosure may also include a combination of a dependent claim with the subject matter of other dependent claims, or a combination of features with other dependent or independent claims. Furthermore, the disclosure may include features of a claim combined with any other independent claim.

The above described embodiments are merely illustrative for the principles of the present disclosure. It is noted that modifications and variations of the arrangements and the details described herein are contemplated as being a part of the disclosure.

What is claimed is:

1. A gas sensing device for sensing a target gas in a gas mixture, the gas sensing device comprising:
- a measurement module configured for obtaining a sampled measurement signal, the sampled measurement signal being responsive to a concentration of the target gas in the gas mixture, the measurement module comprising a gas sensor;
- a compensation module configured for compensating the sampled measurement signal using offset information to obtain a compensated measurement signal; and
- a processing module configured for
  - detecting samples of the sampled measurement signal, a sample of which fulfils a set of one or more criteria, wherein a first criterion of the set of criteria is fulfilled if, according to an evaluation of the sampled measurement signal, the sample is associated with a concentration of the target gas below a threshold, and
  - updating the offset information based on samples which fulfills the set of criteria, wherein the processing module is configured to continuously update a sensor baseline of the gas sensor with the offset information throughout a measurement period whenever a sample, from the samples of the sampled measurement signal, associated with the concentration of the target gas below the threshold is detected.

2. The gas sensing device according to claim 1, wherein the processing module is configured for performing the evaluation of the sampled measurement signal with respect to a characteristic of the compensated measurement signal, and wherein the first criterion is fulfilled if the characteristic indicates that the sample is associated with a concentration of the target gas below the threshold.

3. The gas sensing device according to claim 2, wherein the processing module is configured for
- determining, for a sample of the compensated measurement signal, a set of features, the features representing respective characteristics of the compensated measurement signal, and
- determining a sensing result based on the set of features using an algorithm,
- wherein the characteristics represented by the features comprise the characteristic.

4. The gas sensing device according to claim 2, wherein the gas sensor comprises a chemo-resistive gas sensing unit, wherein the sampled measurement signal is indicative of a resistance of the chemo-resistive gas sensing unit, and wherein the characteristic is a sign or a magnitude of the compensated measurement signal.

5. The gas sensing device according to claim 4, wherein a second criterion of the set of criteria is fulfilled if the sample represents an extremum of the compensated measurement signal with respect to the characteristic.

6. The gas sensing device according to claim 2, wherein the measurement module gas sensor comprises at least one chemo-resistive gas sensing unit for sensing the target gas, wherein the measurement module is configured for obtaining the sampled measurement signal using the chemo-resistive gas sensing unit, wherein the measurement module comprises a thermal heater configured for heating the chemo-resistive gas sensing unit according to a periodic temperature profile, and wherein the characteristic is a frequency domain characteristic, and wherein the processing module is configured for performing the evaluation of the sampled measurement signal on a sequence of samples of the compensated measurement signal with respect to the frequency domain characteristic.

7. The gas sensing device according to claim 1, wherein the processing module is configured for determining a temporal model for the offset information based on a plurality of detected samples which fulfil the set of criteria; and updating the offset information based on the temporal model.

8. The gas sensing device according to claim 7, wherein the temporal model is based on a polynomial function, and wherein the processing module is configured to determine parameters of the polynomial function based on the plurality of detected samples which fulfil the set of criteria.

9. The gas sensing device according to claim 1, wherein the processing module is configured for performing the evaluation of the sampled measurement signal by using an algorithm to determine a sensing result, and wherein the first criterion is fulfilled if the sensing result indicates that the concentration of the target gas is below the threshold.

10. The gas sensing device according to claim 9, wherein the gas sensor comprises a chemo-resistive gas sensing unit, wherein the sampled measurement signal is indicative of a resistance of the chemo-resistive gas sensing unit, and wherein a second criterion of the set of criteria is fulfilled if a value of the sample of the sampled measurement signal indicates that the resistance of the chemo-resistive gas sensing unit is above a further threshold.

11. The gas sensing device according to claim 1, wherein the compensation module is configured for compensating the sampled measurement signal based on a difference between a value of the sampled measurement signal and an offset value indicated by the offset information.

12. The gas sensing device according to claim 1, wherein the processing module is configured for using an algorithm to determine a sensing result based on the compensated measurement signal.

13. The gas sensing device according to claim 1, wherein the gas sensor comprises at least one chemo-resistive gas sensing unit for sensing the target gas, and wherein the measurement module is configured for obtaining the sampled measurement signal using the chemo-resistive gas sensing unit.

14. The gas sensing device according to claim 1, wherein the sampled measurement signal comprises a sequence of samples, and wherein the processing module is configured for checking, for a subset of samples of the sequence, or for all samples of the sequence, whether the set of one or more criteria is fulfilled.

15. A method for sensing a target gas in a gas mixture, the method comprising:

obtaining a sampled measurement signal with a gas sensor, the sampled measurement signal being responsive to a concentration of the target gas in the gas mixture;

compensating the sampled measurement signal using offset information to obtain a compensated measurement signal;

detecting, samples of the sampled measurement signal, a sample of which fulfils a set of one or more criteria, wherein a first criterion of the set of criteria is fulfilled if, according to an evaluation of the sampled measurement signal, the sample is associated with a concentration of the target gas below a threshold; and continuously updating a sensor baseline of the gas sensor with the offset information throughout a measurement period whenever a sample, from the samples of the sampled measurement signal, associated with the concentration of the target gas below the threshold is detected.

16. The method according to claim 15, further comprising:

performing the evaluation of the sampled measurement signal with respect to a characteristic of the compensated measurement signal, and wherein the first criterion is fulfilled if the characteristic indicates that the sample is associated with a concentration of the target gas below the threshold.

17. The method according to claim 16, further comprising:

determining, for a sample of the compensated measurement signal, a set of features, the features representing respective characteristics of the compensated measurement signal, and determining a sensing result based on the set of features using an algorithm, wherein the characteristics represented by the features comprise the characteristic.

18. A gas sensing device for measuring a target gas in a gas mixture, the gas sensing device comprising a processor having access to memory media storing instructions executable by the processor for:

obtaining a sampled measurement signal with a gas sensor, the sampled measurement signal being responsive to a concentration of the target gas in the gas mixture;

compensating the sampled measurement signal using offset information to obtain a compensated measurement signal;

detecting, samples of the sampled measurement signal, a sample of which fulfils a set of one or more criteria, wherein a first criterion of the set of criteria is fulfilled if, according to an evaluation of the sampled measurement signal, the sample is associated with a concentration of the target gas below a threshold;

continuously updating a sensor baseline with the offset information based on a sample, from the samples of the sampled measurement signal, associated with the concentration of the target gas below the threshold; and performing the evaluation of the sampled measurement signal with respect to a characteristic of the compensated measurement signal, and wherein the first criterion is fulfilled if the characteristic indicates that the sample is associated with a concentration of the target gas below the threshold.

19. The gas sensing device according to claim 18, wherein the gas sensor comprises a chemo-resistive gas sensing unit, wherein the sampled measurement signal is indicative of a resistance of the chemo-resistive gas sensing unit, and wherein the characteristic is a sign or a magnitude of the compensated measurement signal.

20. The gas sensing device according to claim 18, further comprising:

determining a temporal model for the offset information based on a plurality of detected samples which fulfil the set of criteria; and updating the offset information based on the temporal model.

* * * * *